United States Patent
Banavar et al.

(10) Patent No.: US 11,783,726 B2
(45) Date of Patent: Oct. 10, 2023

(54) METHODS FOR AND COMPOSITIONS FOR DETERMINING FOOD ITEM RECOMMENDATIONS

(71) Applicant: Viome Life Sciences, Inc., Bellevue, WA (US)

(72) Inventors: Guruduth S. Banavar, Pelham Manor, NY (US); Helen Messier, Cupertino, CA (US); Reza Basseda, Palisades Park, NJ (US); Debra Heald, Calgary (CA); Alla Perlina, San Diego, CA (US)

(73) Assignee: VIOME LIFE SCIENCES, INC., Bellevue, WA (US)

( * ) Notice: Subject to any disclaimer, the term of this patent is extended or adjusted under 35 U.S.C. 154(b) by 0 days.

(21) Appl. No.: 17/850,818

(22) Filed: Jun. 27, 2022

(65) Prior Publication Data

US 2022/0335852 A1    Oct. 20, 2022

Related U.S. Application Data

(63) Continuation of application No. 17/283,934, filed as application No. PCT/US2019/055270 on Oct. 8, 2019.

(Continued)

(51) Int. Cl.
*G09B 19/00* (2006.01)
*A23L 33/00* (2016.01)
(Continued)

(52) U.S. Cl.
CPC .......... *G09B 19/0092* (2013.01); *A23L 33/30* (2016.08); *C12Q 1/6869* (2013.01);
(Continued)

(58) Field of Classification Search
CPC .... G09B 19/00; G09B 19/0092; G09B 23/28; C12N 15/1003
See application file for complete search history.

(56) References Cited

U.S. PATENT DOCUMENTS

| 5,966,712 A | 10/1999 | Sabatini et al. |
| 2003/0091964 A1* | 5/2003 | Yeager ................... G06Q 30/02 708/133 |

(Continued)

FOREIGN PATENT DOCUMENTS

| WO | 2015027057 A1 | 2/2015 |
| WO | 2017093337 A1 | 6/2017 |

(Continued)

OTHER PUBLICATIONS

Shi, Yanmei et al. Integrated metratranscriptomic and metagenomic analyses of stratified microbial assemblages in the open ocean, The ISME Journal (2011) 5, 999-1013 (Supplemental Materials).

(Continued)

*Primary Examiner* — Kurt Fernstrom
(74) *Attorney, Agent, or Firm* — Naira Simmons; FisherBroyles, LLP

(57) ABSTRACT

Provided are methods and compositions for providing one or more food item recommendations for an individual. Methods can include determining an individual set of conditions from an overall set of conditions for the individual. Methods also include generating recommendations involving consumption of food, supplement and/or ingredients to affect the one or more biological conditions.

17 Claims, 5 Drawing Sheets

Related U.S. Application Data

(60) Provisional application No. 62/834,284, filed on Apr. 15, 2019, provisional application No. 62/742,873, filed on Oct. 8, 2018.

(51) Int. Cl.
```
G16H 10/40      (2018.01)
G16H 20/60      (2018.01)
G16B 20/00      (2019.01)
G16B 30/00      (2019.01)
C12Q 1/6869     (2018.01)
G09B 5/02       (2006.01)
```

(52) U.S. Cl.
CPC ............ *G09B 5/02* (2013.01); *G16B 20/00* (2019.02); *G16B 30/00* (2019.02); *G16H 10/40* (2018.01); *G16H 20/60* (2018.01); *A23V 2002/00* (2013.01)

(56) References Cited

U.S. PATENT DOCUMENTS

| | | | |
|---|---|---|---|
| 2009/0275002 A1* | 11/2009 | Hoggle | G16H 20/60 707/999.1 |
| 2011/0053121 A1* | 3/2011 | Heaton | A61B 5/1495 600/365 |
| 2011/0091842 A1* | 4/2011 | Dugan | G09B 5/02 709/219 |
| 2011/0166881 A1* | 7/2011 | Brazzo | G06Q 30/02 705/3 |
| 2011/0208617 A1* | 8/2011 | Weiland | G06Q 30/0641 705/27.1 |
| 2011/0294128 A1* | 12/2011 | Peytavi | C12N 1/06 536/25.4 |
| 2013/0157233 A1 | 6/2013 | Leville | |
| 2013/0216982 A1* | 8/2013 | Bennett | G09B 19/0092 434/127 |
| 2014/0030703 A1* | 1/2014 | Fischer | C12Q 1/686 435/6.12 |
| 2014/0335522 A1* | 11/2014 | Menard | C12Q 1/6806 435/6.15 |
| 2015/0079551 A1* | 3/2015 | Egan | G09B 19/0092 434/127 |
| 2015/0294593 A1* | 10/2015 | Schoen | G09B 19/0092 434/127 |
| 2015/0294594 A1* | 10/2015 | Pacione | A61B 5/4812 434/127 |
| 2015/0371553 A1* | 12/2015 | Vento | G09B 19/0092 434/127 |
| 2016/0030127 A1 | 2/2016 | Choi et al. | |
| 2016/0035248 A1* | 2/2016 | Gibbs | G06T 7/0002 434/127 |
| 2016/0098942 A1* | 4/2016 | Messier | G09B 5/00 434/127 |
| 2016/0140869 A1* | 5/2016 | Kuwahara | G09B 19/0092 434/127 |
| 2016/0166195 A1* | 6/2016 | Radecka | A61B 5/112 600/595 |
| 2016/0232311 A1 | 8/2016 | Segal et al. | |
| 2016/0253922 A1* | 9/2016 | Kremen | G09B 19/0092 434/127 |
| 2016/0263166 A1 | 9/2016 | Elinav et al. | |
| 2016/0379520 A1* | 12/2016 | Borel | G09B 19/0092 434/127 |
| 2017/0262948 A1* | 9/2017 | Bhatt | G06Q 50/12 |
| 2017/0286619 A1 | 10/2017 | Apte et al. | |
| 2018/0122510 A1 | 5/2018 | Apte et al. | |
| 2018/0230451 A1* | 8/2018 | Selden | C12N 15/1003 |
| 2018/0240359 A1 | 8/2018 | Hujsak | |
| 2018/0261329 A1* | 9/2018 | Blander | A61B 5/742 |
| 2019/0055541 A1* | 2/2019 | Min | C12N 1/066 |
| 2019/0142875 A1 | 5/2019 | Elinav et al. | |
| 2019/0251861 A1* | 8/2019 | Wolf | G16H 20/60 |
| 2020/0066181 A1* | 2/2020 | Hadjigeorgiou | G16H 20/60 |
| 2021/0004891 A1* | 1/2021 | Abutair | G06F 16/287 |
| 2021/0233615 A1 | 7/2021 | Banavar et al. | |
| 2021/0332418 A1 | 10/2021 | Vuyisich et al. | |
| 2021/0398449 A1 | 12/2021 | Banavar et al. | |
| 2022/0102000 A1 | 3/2022 | Segal et al. | |
| 2022/0130276 A1 | 4/2022 | Banavar et al. | |
| 2022/0335853 A1 | 10/2022 | Banavar et al. | |

FOREIGN PATENT DOCUMENTS

| | | |
|---|---|---|
| WO | 2017100688 A1 | 6/2017 |
| WO | 2018036503 A1 | 3/2018 |
| WO | 2018160899 A1 | 9/2018 |
| WO | 2018237209 A1 | 12/2018 |
| WO | 2019209753 A1 | 10/2019 |
| WO | 2020051559 A1 | 3/2020 |
| WO | 2020076874 A1 | 4/2020 |
| WO | 2020168015 A1 | 8/2020 |

OTHER PUBLICATIONS

Supplementary European Search Report for EP20755298 dated Jan. 9, 2023; date of completion Sep. 23, 2022, 22 pages.
U.S., Office Action for U.S. Appl. No. 17/855,666 dated Jan. 30, 2023, 19 pages [Co-Owned].
Banavar et al. "The New Era of AI will Revolutionize our Wellness," Proceedings of the 8th Balkan Conference of Informatics, Sep. 20, 2017, pp. 2-2.
Breitwieser, Florian, et al. "A review of methods and databases for metagenomic classification and assembly," Briefings in Bioinformatics, vol. 20, Issue 4, Jul. 2019, pp. 1125-1136, doi.org/10.1093/bib/bbx120, Published: Sep. 23, 2017.
European Search Report for Application No. 19857515, dated May 6, 2022, 8 pages (Dated of Completion Apr. 27, 2022).
European Search Report for Application No. 19870574 dated May 23, 2022, 10 pages.
Franzosa et al. "Sequencing and beyond: integrating molecular 'omics' for microbial community profiling" Nature Reviews Microbiology. Apr. 27, 2015 (Apr. 27, 2015) vol. 13, p. 360-372.
Gurry, et al., "Predictability and Persistence of Prebiotic Dietary Supplementation in a Healthy Human Cohort", Scientific Reports, Aug. 23, 2018, vol. 8, 12699 (pp. 1-13).
Halfvarson et al. "Dynamics of the Human Gut Microbiome in Inflammatory Bowel Disease," Nat Microbiol, Feb. 13, 2017, vol. 2, pp. 1-15.
Hatch, A et al. A Robust Metatranscriptomic Technology for Population-Scale Studies of Diet, Gut Microbiome, and Human Health. International Journal of genomics. Oct. 1, 2019, vol. 2019, No. 1718741; pp. 1-9; entire document; DOI: 10.1155/2019/1718741.
International Search Report and Written Opinion dated Jun. 26, 2020, for PCT application No. PCT/US2020/018013.
International Search Report and Written Opinion for Application No. PCT/US19/55270, dated Jan. 2, 2020, 11 pages.
International Search Report and Written Opinion for International Patent Application No. PCT/US2019/028590 mailed on Jul. 23, 2019, 23 pages.
International Search Report and Written Opinion for PCT/US19/50102, dated Jan. 9, 2020, 15 pages.
Korem, T. et al. Bread affects clinical parameters and induces gut microbiome-associated personal glycemic responses, Cell Metabolism, vol. 25, No. 6, Jun. 1, 2017; pp. 1243-1253.
Lechatlier et al. "Richness of Human Gut Microbiome Correlates with Metabolic Markers," Nature, Aug. 28, 2013, vol. 500, No. 7464, pp. 541-546.
Lee et al. "Metaproteomic analysis of human gut microbiota: where are we heading?", Journal of Biomedical Science, vol. 24, Jun. 12, 2017, pp. 1-8, XP055700633.
Mendes-Soares, et al., "Assessment of a Personalized Approach to Predicting Postprandial Glycemic Responses to Food Among Individuals Without Diabetes", JAMA Network Open, Feb. 8, 2019, vol. 2, No. 2, e188102 (pp. 1-13).

(56) References Cited

OTHER PUBLICATIONS

Spritzler "How to Choose the Best Probiotic Supplement" Healthline. Jan. 21, 2017 22(Jan. 21, 2017) ; p. 7, para 2.
Supplementary European Search Report for European Application No. 19857575, dated Apr. 27, 2022, 8 pages.
Supplementary Partial European Search Report for EP20755298 dated Oct. 5, 2022, 24 pages.
Tily Hal et al.; "Gut microbiome activity contributes to individual variation in glycemic response in adults," bioRxiv, Aug. 22, 2019, SP055923516; retrieved from the internet; URL:http://www.biorxiv.org/content/biorxiv/early/2019/08/24/641019.full.pdf, 10 pages.
Zeevi, et al., "Personalized Nutrition by Prediction of Glycemic Responses", Cell, Nov. 19, 2015, vol. 163, No. 5 (pp. 1079-1094).

* cited by examiner

500 Receive biological sample from a subject; (e.g., gut microbiome)

510 Sequence nucleic acids from biological sample to produce nucleic acid sequence data;

520 Collect phenotypic data from the subject;

530 Determine:
Phenotypic conditions in the subject from the phenotypic data and
Functional activity conditions in the subject from the nucleic acid sequence data;

540 Access a knowledge base that includes for each of a plurality of food items desirability ranking of the food for each of the phenotypic conditions and functional activity conditions present in the subject;

550 Using a recommendation engine, execute logic to produce a recommendation for each food item for the subject; and 560 Output the food recommendations to an electronic device accessible by the subject.

FIG. 5

METHODS FOR AND COMPOSITIONS FOR DETERMINING FOOD ITEM RECOMMENDATIONS

REFERENCE TO RELATED APPLICATIONS

This application is a continuation of U.S. application Ser. No. 17/283,934, filed Apr. 8, 2021, which is a 371 National Phase application claiming benefit of PCT/US2019/055270, filed Oct. 8, 2019, which claims the benefit of the priority date of U.S. application 62/742,873, filed Oct. 8, 2018, and U.S. application 62/834,284, filed Apr. 15, 2019, the contents of which are incorporated by reference in their entirety.

BACKGROUND

Current methods of providing food and/or supplement recommendations are often based on only one condition, and do not take into account multiple conditions that may be present in an individual, nor do they take into account multiple effects of a given food on the conditions in the individual. Improved methods and compositions for providing food and/or supplement recommendations to an individual are needed.

SUMMARY

Provided herein is a method of determining recommendations of desirability of a plurality of different foods for an individual, wherein the individual has an individual set of biological conditions comprising at least 1 biological condition, and wherein the recommendation for each food is based on its predicted effect on the at least 1 biological condition. The individual set of biological conditions can comprises at least 2 biological conditions, and the recommendation for each food can be based on combining recommendations for the food for each of the two conditions. The individual set of biological conditions can comprise at least 3 biological conditions, and the recommendation for each food can be based on combining recommendations for the food for each of the 3 conditions. The individual set of biological conditions can comprise at least 4 biological conditions, and the recommendation for each food can be based on combining recommendations for the food for each of the 4 conditions. The individual set of biological conditions can comprise at least 5 biological conditions, and wherein the recommendation for each food is based on combining recommendations for the food for each of the 5 conditions. The condition or conditions can be determined from an overall set of biological conditions. The plurality of different foods can comprise at least 2, 5, 10, 20, 30, 40, 50, 70, 100, 120, 150, 170, 200, 250, or 300 different foods. The recommendation of desirability of the plurality of different food can comprise at least 2, 3, or 4 discrete values of desirability, wherein the values are in order of decreasing desirability. When more than one biological condition is examined, if a recommendation of desirability of a food for any of the biological conditions examined is different from the others, a final recommendation can be determined by choosing the most restrictive recommendation. In certain cases, the individual set of biological conditions comprises at least 2, 3, 4, 5, 6, 7, 8, 9 or 10 biological conditions, and the recommendation for each food can based on its predicted effect on at least some of the biological conditions in the individual set of biological conditions, for example, the recommendation for each food can be based on its predicted effect on at least ¼, ½ or ¾ of the biological conditions in the individual set of biological conditions. The individual can be determined to have an individual set of biological conditions based on phenotype and microbiome information for the individual. The phenotype information can be obtained in a process comprising determining responses for the individual to a questionnaire. The microbiome information can be obtained from a sample from the individual, such as a stool sample. The microbiome information can comprise transcriptome information. The microbiome information can comprise information regarding viruses in the microbiome. The method can include determining a recommendation for desirability of consumption of a first food of the plurality of foods for the individual comprises performing at least one of (i) predicting an effect of macronutrient content of the first food on a first biological condition in the individual and determining a first recommendation based on the predicted effect of macronutrient content of the food; (ii) predicting an effect of one or more specific compounds in the first food on the first biological condition in the individual and determining a second recommendation based on the predicted effect of the one or more specific compounds; and (iii) predicting an effect of the first food on a microbiome of the individual, and determining a third recommendation based on the predicted effect on the microbiome. In certain embodiments, the method comprises performing at least two of steps (i)-(iii). In certain embodiments the method comprises performing all of steps (i)-(iii); in some cases, steps (i), (ii), and (iii) are performed in sequential order. In certain embodiments of the method, after a food is given a first recommendation after step (i), then step (ii) is performed and the food is given a second recommendation, wherein the second recommendation can be the same as the first recommendation or an upgrade or downgrade of the first recommendation, then step (iii) is performed and the food is given a third recommendation, wherein the third recommendation can be the same as the second recommendation or an upgrade or downgrade of the second recommendation. In certain embodiments, desirability for consumption of a food can have at least 2, 3, or 4 values, which can be graded in terms of desirability. The method can further comprise performing one or more of steps (i)-(iii) for a second biological condition, where the second biological condition is different from the first, and determining a recommendation for desirability of consumption of the food for the second biological condition. At least one of steps (i)-(iii) can be performed for the second biological condition. At least two of steps (i)-(iii) can be performed for the second biological condition. At least one of steps (i)-(iii) is performed for the second biological condition, which in some cases can be performed sequentially. The method can further comprise combining the recommendations for desirability of consumption of the food for the first biological condition and for the second biological condition to determine a combined desirability for consumption of the food; in certain cases, the combining comprises determining whether one recommendation for desirability is more restrictive than the other, and, if so, determining that the combined desirability for consumption of the food is the more restrictive desirability. The method can further comprise performing one or more of steps (i)-(iii) for a third biological condition, where the third biological condition is different from the first and second biological conditions, and determining a recommendation for desirability of consumption of the food for the third biological condition. At least one of steps (i)-(iii) can be performed for the third biological condition. At least two of steps (i)-(iii) can be performed for the third biological condition. All three of steps (i)-(iii) can be performed for the third biological condition; in certain embodiments the steps are performed sequentially. The method can further comprise combining the recommendations for desirability of consumption of the food for the first, second, and third biological conditions to determine a combined desirability for consumption of the food. The method can further comprise determining which if any, of the recommendations for desirability of consumption of the food is most restrictive, and, if so, determining that the combined desirability for consumption of the food is the most restrictive desirability. The method can further comprising performing steps (i)-(iii) for a fourth biological condition, where the fourth biological condition is different from the first, second, and third biological conditions, and determining a recommendation for desirability of consumption of the food for the fourth biological condition. In certain embodiments, at least one of steps (i)-(iii) is performed for the fourth biological condition. In certain embodiments, at least two of steps (i)-(iii) is performed for the fourth biological condition. In certain embodiments, all three of steps (i)-(iii) is performed for the fourth biological condition; in certain embodiments, steps (i)-(iii) are performed sequentially. The method may further comprise combining the recommendations for desirability of consumption of the food for the first, second, third, and fourth biological conditions to determine a combined desirability for consumption of the food, for example determining which if any, of the recommendations for desirability of consumption of the food is most restrictive, and, if so, determining that the combined desirability for consumption of the food is the most restrictive desirability. In certain embodiments, any of the above methods may further be used to determine a recommendation for desirability of consumption of a second food from the plurality of foods, wherein the second food is different from the first, and where the method comprises performing one or more of steps (i)-(iii) for the second food, for at least 1, 2, 3, 4, or 5 biological conditions from the individual set of biological conditions. For any of the methods above, one or more of steps (i)-(iii) are performed for at least 2, 5, 10, 20, 50, 100, 150, 200, 250, or 300 different foods. For any of the methods above, one or more of the foods are classed as part of a food group and the prediction of one or more of steps (i), (ii) and/or (iii) is based on the food group. The method may further comprise providing an explanation for the recommendations for at least some of the foods to the individual, where the explanation is determined from results of one or more steps of analysis of the food and its effect or effects on one or more conditions of the individual; the recommendation can be provided as text suitable for understanding by a layman.

Provided herein is a method of determining a set of food recommendations for an individual comprising (i) determining an individual set of one or more biological conditions for the individual from an overall set of biological conditions by combining phenotype and microbiome information for the individual; and (ii) determining the food recommendations for the individual based on the predicted effects of foods and/or food groups on one or more of the conditions for the individual. The microbiome information can include transcriptome information. The microbiome information can include taxa information and gene expression information. The microbiome information can include one, two, three, four or all of bacterial, virus information, archaebacteria, or protest information. The predicted effects can comprise macronutrient effects, specific compound effects, microbiome effects, or any combination thereof. If predicted effects of a food or food group lead to different recommendations for a food for different conditions, the most restrictive recommendation can be chosen as the final recommendation.

Provided herein is a method of determining a recommendation for desirability of consumption of a first food for an individual comprising performing at least one of (i) predicting an effect of macronutrient content of the first food on a first biological condition in the individual and determining a first recommendation based on the predicted effect of macronutrient content of the food; (ii) predicting an effect of specific compound content of the first food on the first biological condition in the individual and determining a second recommendation based on the predicted effect, wherein the second recommendation can be the same as or different from the first recommendation, depending on the micronutrient effect; and (iii) predicting an effect of the first food on a microbiome of the individual, and determining a third recommendation based on the predicted effect, wherein the third recommendation can be the same as or different from the second recommendation, depending on the microbiome effect. The microbiome information can include information regarding the presence or absence, quantity, or other characteristic of one, two, three, four, or all of bacteria, viruses, archaebacteria, fungi, or protists that may be affected by the first food. The method can comprise performing at least two of steps (i)-(iii). The method can comprise performing all of steps (i)-(iii), for example, performing steps (i), (ii), and (iii) in sequential order. The recommendation for desirability for consumption of a food can have at least 2, 3, or 4 values, which can be graded in terms of desirability. The method can further comprise performing one, two, or all of steps (i)-(iii) for a second biological condition, where the second biological condition is different from the first, and determining a recommendation for desirability of consumption of the food for the second biological condition. The recommendation for desirability of consumption of the food for the first biological condition can be compared to that for the second biological condition to determine which, if either, is more restrictive, and determining a final recommendation for desirability of the food that is the more restrictive desirability. The method can further comprise performing one, two, or all of steps (i)-(iii) for a third biological condition, where the third biological condition is different from the first and second biological conditions, and determining a recommendation for desirability of consumption of the food for the third biological condition. The recommendations for desirability of consumption of the food for the first, second, and third biological conditions can be compared to determine which, if any, is most restrictive, and determining a final recommendation for desirability of the food that is the most restrictive desirability. The method can further comprise performing one, two, or all of steps (i)-(iii) for a fourth biological condition, where the fourth biological condition is different from the first, second, and third biological conditions, and determining a recommendation for desirability of consumption of the food for the fourth biological condition. The recommendations for desirability of consumption of the food for the first, second, third, and fourth biological conditions can be compared to determine which, if any, is most restrictive, and determining a final recommendation for desirability of the food that is the most restrictive desirability. The method can further comprise performing one, two, or all of steps (i)-(iii) for a fifth biological condition, where the fifth biological condition is different from the first, second, third, and fourth biological conditions, and determining a recommendation for desirability of consumption of the food for the fifth biological condition. The recommendations for desirability of consumption of the food for the first, second, third, fourth, and fifth biological conditions can be compared to determine which, if any, is most restrictive, and a final recommendation for desirability of the food can be determined that is the most restrictive desirability. The method can further comprise determining a recommendation for desirability of consumption of a second food, wherein the second food is different from the first, by performing one, two, or all steps (i)-(iii) for the second food, for the first, second, third, fourth, or fifth condition, or any combination thereof, and combining recommendations for different conditions if the recommendations differ. In any of the methods of this paragraph, one, two, or all of steps (i)-(iii) can be performed for at least 2, 5, 10, 20, 50, 100, 150, 200, 250, or 300 different foods. In any of the methods of this paragraph, a food can be classed as part of a food group and the prediction of (i), (ii) and/or (iii) can be based on the food group. For any of the methods of this paragraph, the method can further comprise providing an explanation for the recommendations for at least some of the foods to the individual, wherein the recommendation is determined from results of one or more steps of analysis of the food and its effect on one or more conditions of the individual. The explanation can be provided as text suitable to layman understanding.

Provided herein is a composition comprising a list of food recommendations for an individual, wherein the recommendations are derived from predicting effects of each food on the list on one or more biological conditions of the individual, wherein the effects comprise one, two, or all of effects of macronutrient content of the food, effects of specific compound effect of the food, and effects of the food on the microbiome of the individual with regard to at least one biological condition of the individual. The list can further comprise, for at least some of the foods, an explanation for the recommendation for the food, wherein the recommendation indicates one or more probable effects of macronutrient and/or specific compound content of the food and/or microbiome interaction with the food, on one or more of the biological conditions, or the effects of one or more conditions, in the individual. The explanation can be in layman's terms. The list can comprise at least 5, 10, 15, 20, 25, 30, 40, 50, 70, 100, 150, 200, 250, or 300 different food recommendations. Each food on the list can be designated a value according to its desirability for the individual, such as one of at least 2, 3, or 4 values for desirability, for example one of values for desirability. In certain embodiments, the foods are chosen from the foods in Table 2.

Provided herein is a method of improving one or more biological conditions in an individual comprising (i) supplying the individual with food, supplement and/or ingredient recommendations, wherein the food, supplement and/or ingredient recommendations are based predicted effects of one or both of macronutrient content, specific compound content of the food or supplement on one or more biological conditions of the individual and, optionally, effect of the food on a microbiome of the individual; and (ii) altering the individual's food, supplement and/or ingredient consumption so that it more closely matches the food, supplement and/or ingredient recommendations. The one or more biological conditions of the individual can be determined by analysis of phenotype information and microbiome information from the individual. Phenotype information can be obtained in a process comprising determining responses for the individual to a questionnaire and microbiome information is obtained from a sample from the individual, such as a stool sample. The microbiome information can comprise transcriptomic information. The microbiome information can comprise taxonomic information and gene expression information. The microbiome information can comprise information regarding one or more biochemical molecules in a sample from the individual. The one or more biochemical molecule can be informative of one or more biochemical activities. The information on biochemical activity can be obtained by a process comprising quantifying an enzymatic activity assay, a growth-inhibition culture, metabolic profiling, or any combination thereof. In certain embodiments, the biochemical molecule is a small molecule, and the small molecule can comprise a metabolite generated by the biochemical activity. The small molecule can comprise a short-chain fatty acid, such as butyrate or propionate. The small molecule can comprise a substrate of the biochemical activity. The food recommendations can comprise a list of foods, each of which has a designation indicating desirability or undesirability of that food for the individual. The designation can have one of at least 2, 3, or 4 values. The food, supplement and/or ingredient recommendations can be produced by a process comprising (i) selecting an individual set of biological conditions for the individual from an overall set of biological conditions based on the individual's phenotype and microbiome information; (ii) determining overall predicted desirability of foods, food groups, and/or supplements on at least part of the individual set of biological conditions for the individual; and (iii) from the results of (ii) determine the food, supplement and/or ingredient recommendations for the individual. The method can further comprise gathering information from the individual regarding phenotype and microbiome after the individual has implemented the recommendations for a period of time, such as one week to one year. After gather the information after the period of time, the method can further comprise altering the food, supplement and/or ingredient recommendations for the individual based on the phenotype and microbiome information gathered after the period of time.

In one aspect provided herein is a method comprising: (a) generating -omic data from a subject; (b) determining, from the -omic data, the presence of one or more biological conditions in the subject; (c) accessing a knowledge base, wherein the knowledge base indicates, for each of a plurality of items selected from foods, supplements and ingredients, a desirability rating of consuming the item for the one or more biological conditions; and (d) for each item, implementing computer logic to determine a final recommendation for the item, wherein the final recommendation is based on the combined desirability ratings for the biological conditions. In one embodiment the subject is a human. In another embodiment the -omic data is generated from a biological sample from the subject. In another embodiment the biological sample comprises a gut microbiome sample or a blood sample. In another embodiment generating -omic data comprises performing high-throughput sequencing on nucleic acids from a sample from the subject to produce sequence data. In another embodiment the functional activity conditions are determined from functional activity scores determined from the -omic data. In another embodiment the functional activity scores are integrative scores comprising more than one type of input data, e. G., KO identifiers, taxonomy identifiers or human gene identifiers. In another embodiment the functional activity scores are non-integrative scores comprising only one type of input data. In another embodiment the -omic data comprises gut microbiome metatranscriptomic data. In another embodiment the biological conditions comprise functional activity conditions. In another embodiment the functional activity conditions include or more of: butyrate production pathways, LPS biosynthesis pathways, methane gas production pathways, sulfide gas production pathways, flagellar assembly pathways, ammonia production pathways, putrescine production pathways, oxalate metabolism pathways, uric acid production pathways, salt stress pathways, biofilm chemotaxis in virulence pathways, TMA production pathways, primary bile acid pathways, secondary bile acid pathways, acetate pathways, propionate pathways, branched chain amino acid pathways, long chain fatty acid metabolism pathways, long chain carbohydrate metabolic pathways, cadaverine production pathways, tryptophan pathways, starch metabolism pathways, fucose metabolism pathways, inflammatory activity, metabolic fitness, digestive efficiency, intestinal barrier health, protein fermentation, gas production, microbial richness, detoxification potential (ability of microbiome to detoxify the body), gut neuro-balance (impact of microbiome on the brain, e.g., by production of neurotransmitters), neurological health, cardiovascular health, hormonal balance, musculoskeletal health, hepatic function, urogenital health, mitochondrial activity, immune function, gastrointestinal health, diabetes, skin conditions, infectious disease, stress response, mitochondrial health, mitochondrial biogenesis, oxidative stress, aging and senescence. In another embodiment the -omic data comprises metatranscriptomic data, and determining functional activity conditions comprises executing computer logic to determine functional activity scores from the metatranscriptomic data. In another embodiment determining comprises: (i) executing computer logic to determine biological pathway scores and taxa activity scores, and (ii) deriving functional activity scores from the biological pathway scores and taxa activity scores. In another embodiment determining biological pathway scores comprises determining activity of functional orthologs (e.g., in a KEGG Orthology). In another embodiment functional activity scores are measured as continuous variables or in categories. In another embodiment a functional activity score outside of a reference range or outside one or more reference categories indicates a functional activity condition. In another embodiment the -omic data comprises phenotypic data used to determine phenotypic conditions. In another embodiment the -omic data comprises both metatranscriptomic data and phenotypic data. In another embodiment the -omic data comprises proteomic, which data is used to determine functional activity conditions. In another embodiment the biological conditions includes at least one condition selected from the conditions of Table 1. In another embodiment a plurality of items in the knowledge base are foods selected from the foods of Table 2. In another embodiment a plurality of items in the knowledge base are supplements selected from the supplements of Table 3. In another embodiment a plurality of items in the knowledge base are ingredients selected from the compounds of Table 4. In another embodiment the desirability ratings for foods comprise a plurality of ratings hierarchically arranged from least desirable to consume for the condition to most desirable to consume for the biological condition. In another embodiment the plurality of desirability ratings is four ratings, wherein two ratings are undesirable ratings (e.g., "avoid" and "minimize", one rating is highly desirable (e.g., "indulge" or "superfood") and another rating is desirable or neutral (e.g., "enjoy"). In another embodiment the desirability ratings for supplements or ingredients comprise a positive recommendation or no recommendation. In another embodiment a plurality of the desirability ratings are based on literature sources and expert curation. In another embodiment the logic determines a final recommendation by prioritizing, first, ratings indicating a negative effect of the item on a condition, and, prioritizing second, ratings indicating a most beneficial effect of the item on a condition. In another embodiment the hierarchy of rating, from least to most beneficial, is 1-4, and the priority of ratings to produce a final recommendation for a plurality of the items is 1>2>4>3 (e.g., "avoid" >"minimize">"superfood">"enjoy"). In another embodiment the method further comprises determining from the -omic data, a predicted glycemic response by the subject to each of one or more items in the knowledge base, which response indicates a glycemic response desirability rating; and incorporating the glycemic response desirability rating in determining the final recommendation for the item. In another embodiment the glycemic response desirability rating is either positive or negative. In another embodiment the method further comprises determining whether the subject has a sensitivity (i.e., an adverse reaction) for an item; and incorporating any adverse reaction in determining the final recommendation for the item.

In another aspect provided herein is a method comprising: (a) generating functional activity scores by: (i) obtaining a gut microbiome sample from a subject; (ii) sequencing nucleic acids from the sample to produce sequence data; (iii) determining from the sequence data, (1) gene (e.g., KEGG Orthology) activity scores; and (2) taxa activity scores; (iv) determining from the gene activity scores and the taxa activity scores, a functional activity score for each of a plurality of functional categories; (b) optionally, generating a glycemic response score for each of a plurality of food items selected from foods, supplements and ingredients by: (i) executing logic that determines a glycemic response score for a subject based on macronutrient content of the food and the subject's gene activity scores and taxa activity scores; (c) optionally, determining food sensitivities in the subject; (d) generating phenotype scores by: (i) obtaining phenotype data from the subject; (ii) determining, from the phenotype data, a phenotype score for each of a plurality of phenotype categories; (d) accessing from computer memory a food database that includes, for each food item and each sub-optimal functional activity and phenotype status, a hierarchical recommendation of the food or supplement; (e) generating an overall hierarchical recommendation for each food or supplement based on combined recommendations of a food for each sub-optimal condition present and, optionally, the predicted glycemic response and/or food sensitivity to the food or supplement.

In another aspect provided herein is a method comprising: a) receiving a biological sample from a subject; b) sequencing nucleic acids from biological sample to produce nucleic acid sequence data; c) collecting phenotypic data from the subject; d) determining phenotypic conditions in the subject from the phenotypic data and functional activity conditions in the subject from the nucleic acid sequence data; e) accessing a knowledge base that includes for each of a plurality of food items desirability ranking of the food for each of the phenotypic conditions and functional activity conditions present in the subject; f) using a recommendation engine, executing logic to produce a recommendation for each food item for the subject; and f) outputting the food recommendations to an electronic device accessible by the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

The following references, which may be relevant to the present disclosure, are incorporated herein by reference: WO 2019/113563; WO 2018/237209; WO 2019/099574; WO 2018/160899; PCT/US2019/028590. PCT/US2019/050102; U.S. Provisional application 62/804,737

BRIEF DESCRIPTION OF THE DRAWINGS

FIG. 5 shows an exemplary flow chart for generating and outputting food recommendations for a subject. The recommendations are based on phenotypic and/or functional activity conditions of the subject determined from phenotypic and nucleic acid sequence data, and processed by logic executed by a recommendation engine.

DETAILED DESCRIPTION

Provided herein are methods and compositions to provide food, supplement and/or ingredient recommendations to an individual. Also provided herein are methods and compositions to determine an individual set of biological conditions for an individual from an overall set of biological conditions. In certain embodiments food recommendations for the individual are based on predicting the effect of foods and/or groups on one or more biological conditions of an individual. In addition, provided herein are methods and compositions of improving one or more biological conditions of an individual by supplying the individual with food, supplement and/or ingredient recommendations, where the food, supplement and/or ingredient recommendations are based on phenotype and microbiome information for the individual, and altering the individual's food, supplement and/or ingredient intake based on the food and/or supplement recommendations.

I. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The section headings used herein are for organizational purposes only and are not to be construed as limiting the subject matter described.

II. Introduction

Provided herein are methods of making personalized food, supplement and/or ingredient (sometimes collectively referred to as "food items" or "items") recommendations (herein, "food recommendations") for a subject. Food recommendations provide a beneficial ranking of each food or supplement for the subject based on biological conditions present in the subject and, optionally, based on the subject's predicted glycemic response to the food and/or the subject's sensitivity to the food. The final recommendation classifies the food according to its effect on the biological conditions, collectively. Rankings are typically hierarchical, from least to most beneficial for the subject to consume. In one model, there are four rankings, including two negative rankings and two positive rankings (or two negative rankings, a neutral ranking and a positive ranking).

Figure 1:
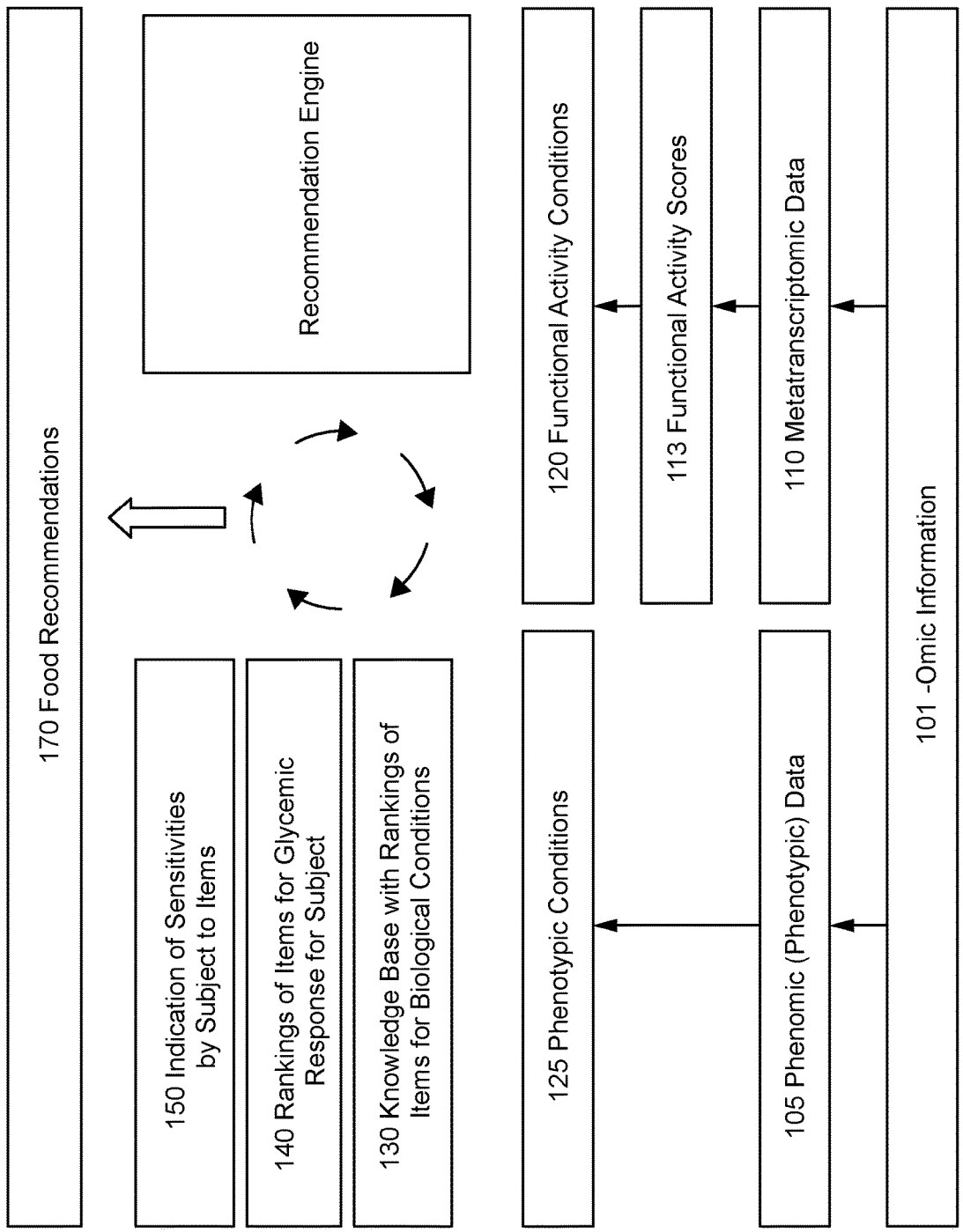
FIG. 1 shows an approach for personalizing food and supplement recommendations for a subject.

Referring to FIG. 1, -omic information is collected for an individual (101). This can include Phenomic (105) and Metatranscriptomic (110) data. Analysis of phenomic data can indicate the presence of phenotypic conditions (125). Bioinformatics can be used to transform metatranscriptomic data into functional activity scores (131). Functional activity scores that are determined to be outside a reference range indicate the presence of a functional activity condition (120). Based on phenotypic conditions and functional activity conditions in the subject, a knowledgebase of foods and conditions (130) is accessed. In addition, subject glycemic response to foods (140) and subject food sensitivities (150) also are determined. A computerized recommendation engine (160) then analyses item desirability rankings for all conditions present in the subject and, optionally, the subject's glycemic response to the item and any subject sensitivity to the item. Using logic, the recommendation engine determines an overall, or final recommendation (Food Recommendation (170)) concerning the food items for the subject.

Biological conditions in a subject include any detectable condition, including, without limitation, phenotypic conditions and functional activity conditions. Phenotypic conditions are based on outward phenotype and subjective responses by the subject, obtained, for example by questionnaire. Functional activity conditions are conditions in which a functional activity score for a functional category are determined to be outside a reference range, e.g., suboptimal. Determination of a functional activity condition can be based on biochemical information collected from the subject. Biochemical data can include data from the subject's microbiome, in particular, from the transcriptome of the microbiome. Transcriptome data can be divided into two parts, biochemical pathway activity data and microbial taxa activity data. In other embodiments, biochemical data can include information from the human transcriptome. Biochemical pathway activity data indicates the activity level of various biochemical pathways in the microbes. Taxa activity data indicates the quantity of various active taxa in the gut microbiome, but their activity levels. These data are, in turn, analyzed to provide a functional activity score to various higher-level functional activities in the subject that involve a plurality of pathways and taxa, such as inflammatory activity.

Predicted glycemic response to a food by a subject also can be calculated based on changes in blood sugar levels by a subject after consumption of a food or supplement.

Sensitivity of a subject to a food or supplement, e.g., allergy, ("food sensitivity") also can be determined by self-reporting from the subject or by testing, e.g., by skin testing.

The food recommendation engine makes use of a food database. The food database includes a table of foods and supplements. For each biological condition, each food or supplement is ranked (e.g., given a recommendation), according the effect consumption of the food or supplement has on the biological condition (e.g., a positive effect=ameliorates the condition, or a negative effect=worsens the condition). Again, rankings can be provided as a number from low to high, such as 1-4, or by a descriptor, such as "avoid" or "indulge".

Effect of a food item on a subject (that is, beneficial or detrimental effect) (which is reported as a food recommendation) is a function of the collective rankings of the food item on each biological condition that the subject has, as optionally modified by glycemic response and food sensitivity data. Accordingly, for a given subject, rankings of a given food on biological conditions present in the subject, optionally, as well as predicted glycemic response and/or food sensitivity, are used to generate the overall recommendation for the food for the subject. Various functions to generate the overall recommendation can be used. For example, the function could make hierarchical recommendations, in which a food or supplement ranked at a certain level for any biological condition trumps all other rankings for the condition. In one such a function, the presence of a single most negative rank (e.g., "avoid") for any present biological condition would give the food a most negative ("avoid") recommendation. If no food has a most negative rank for any condition present, the presence of a single less negative rank (e.g., "minimize") for any present biological condition would give the food a less negative (e.g., somewhat negative) ("minimize") recommendation. If no food has a most negative or less negative rank for any condition present, the presence of a single most positive rank (e.g., "superfood" or "indulge") for any present biological condition would give the food a most positive ("superfood") recommendation. If no food has any of the aforementioned ranks, a neutral or mildly positive rank (e.g., "enjoy") is assigned to the food for the subject. These rankings can be informed by predicted glycemic response and/or food sensitivity. For example, a high glycemic response (which is a negative response) would cap the recommendation to no better than a negative or less negative ranking, while a low glycemic response (which is a positive response) would not alter the recommendation based on condition ranking, or would increase the ranking by a rank. Similarly, presence of a sensitivity to a food could result in a veto, automatically ranking the food at the least beneficial level.

III. Biological Conditions

Typically, the methods and compositions described herein utilize information regarding one or more biological conditions for an individual. An individual may be a member of a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of Drosophila, a species of Xenopus, a species of horse, and a human. In certain embodiments, the individual is a human.

Biological conditions refer generally to the presence of any suboptimal or pathologic health or wellness condition. A phenotype condition is determined to be present when phenotypic data, alone or in combination, indicates the condition. A functional activity condition is determined to be present when a functional activity score is determined to be suboptimal.

Data used in the creation of the recommendations described herein typically comprise large data sets including thousands, tens of thousands, hundreds of thousands or millions of individual measurements taken from or about a subject, typically at the systems biology level. The data can be derived from one or more (typically a plurality) different biological system components. These biological system components, also referred to herein as "feature groups", include, without limitation, the genome (genomic), the epigenome (epigenomic), the transcriptome (transcriptomic), the proteome (proteomic), the metabolome (metabolomic), the organismal cellular lipid components (lipidome), organismal sugar components of complex carbohydrates (glycomic), the proteome and/or genome of the immune system (immunomics) component of a system, organism phenotype (phenome, phenomic, phenotypic) and environmental exposure (exposome). (Generally referred to herein as "-omic" data or information.)

Biological conditions discussed herein may be determined by any suitable means. In certain embodiments, biological conditions are determined from -omic data, including any of the feature groups discussed above. In certain embodiments the -omic data comprises phenotype and/or microbiome information. Alternatively, the omic data can include proteomic data. An individual set of biological conditions for an individual may be chosen from an overall set of biological conditions, based on phenotype and/or microbiome information for the individual. Exemplary biological conditions are shown in TABLE 1.

TABLE 1

Exemplary Biological conditions

Abdominal Weight
Acne
Attention Deficit Disorder
Allergy
Allergy ENT Condition
Allergy Lung Condition
Allergy Skin Condition
Anxiety
AutoImmune
Autoimmune Gut Condition
Autoimmune Joint Condition
Autoimmune Skin Condition
Cardiovascular Condition
Depression
Diverticular Condition
Dysbiosis
DysGlycemia (hyperglycemia)
Dysmotility TABLE 1-continued Exemplary Biological conditions ENT Condition
Eye Condition
Female Hormone Condition
Food Reaction
GERD
GI Inflammation
Headache Condition
HypoGlycemia
HypoThyroid Condition
Infection Condition
Insomnia
Leaky Gut Condition
Liver Condition
Lung Condition
Male Hormone Condition
Muscle Condition
Nerve Condition
Nutritional Deficiency
Obese
Overweight
Small Intestinal Bacterial Overgrowth
Thyroid Condition Provided herein are methods and compositions for determining a set of biological conditions for an individual. The individual set of biological conditions can be determined based on combined phenotype and microbiome information for the individual, and can include at least 1, 2, 3, 4, 5, 6, 7, 8, 9, 10, 11, 12, 13, 14, 15 or more than 15 conditions. The process of determining an individual's set of biological conditions may include determining which conditions from an overall set of biological conditions the individual has; the overall set of biological conditions can be any suitable set, and can include at least 1, 2, 3, 4, 5, 6, 7, 8, 9, 10, 11, 12, 13, 14, 15, 17, 20, 25, 30, 35 or more than 35 conditions. An exemplary overall set of biological conditions is provided in TABLE 1.

A. Phenotype Information

Methods and compositions herein can utilize phenotype information for an individual. Any suitable method of determining phenotype information for the individual may be used. Exemplary methods include examination of physical or medical records, one or more interviews with the individual and/or others, examination of the individual, and use of questionnaires.

In certain embodiments, one or more questionnaires are used, where responses to the one or more questionnaires for the individual are used to partially or completely determine phenotype information for the individual, in particular, as related to biological conditions, for example biological conditions in an overall set of conditions. The questionnaire or questionnaires may include any suitable number of queries, for example, at least 5, 10, 15, 20, 25, 30, 35, 40, 45, 50, 55, 60, 65, 70, or over 70 questions. Responses to questions can be open-ended (e.g., the individual may provide a written response to a question without limit to content of the response, such as a written answer to a question such as "What are your health goals?"), questions with specific answers (e.g., "what medications do you take," "what is your hip circumference in inches" and the like) or questions where the answer can be selected from a limited number of options, or a combination. Limited option questions include yes/no questions, true/false questions, questions that require selection of one or more response from a limited number of responses, which can be non-numerical responses (e.g., "what is your ethnicity," with responses limited to "American Indian or Alaskan Native," "Southeast Asian," "South Asian," "Asian," "Black or African American," "Native Hawaiian or other Pacific Islander," "Caucasian/White," "Hispanic or Latino," or "Other") or numerical responses (e.g., "How many cups of coffee do you drink each day," with responses limited to 0, 1, 2, 3, 4, 5, 6, 7, 8, 9, or 10+; or "how often have you been bothered by a certain symptom (such as headache, or fatigue, or pain or aches in joints, etc.) in the past four weeks," with the answers limited to "none," "a little," or "a lot," etc.), or any other suitable question type that provides information useful in determining a biological condition.

Any suitable method of determining phenotype information from responses to the questionnaire(s), in particular, information regarding an individual set of biological conditions for an individual, may be used. For example, a first biological condition may be assessed by examining the responses to a first subset of questions in the questionnaire(s); the questions in a subset may be weighted so that answers to some questions count more than others. Specific responses to individual questions in the first subset may be assigned specific numerical values, which can be adjusted according to the weight of the question, then the numerical values for all responses in the first subset are totaled to give a phenotype score for the first biological condition. A similar procedure may be followed to assess a second, different biological condition in the individual, using a second subset of questions in the questionnaire(s) to provide a phenotype score for the second biological condition; the second subset of questions may be the same as or different from the first subset. The process may be repeated for any suitable number of biological conditions; when biological conditions for an individual are determined from an overall set of biological conditions, the upper limit will, of course, be the number of biological conditions in the overall set (or fewer, if some of the biological conditions in the overall set are mutually exclusive). Thus, the process can be repeated for at least 2, 3, 4, 5, 6, 7, 8, 9, 10, 12, 15, 17, 20, 22, 25, 30, or 35 conditions, to produce the same number of phenotype scores; each different biological condition is assessed with reference to responses to its own specific subset of questions, which may be the same as or different from subsets for other biological conditions. Questions may belong to more than one subset for more than one biological condition, or may belong to only one subset.

Phenotypic information can be obtained, for example, from subject responses to questionnaires, or from a chat bot that interacts with the subject through natural language conversations. Such questionnaires may gather information on traits such as age, sex, weight, blood type, headaches, faintness, dizziness, insomnia, watery or itchy eyes, swollen, red or sticky eyelids, bags or dark circles under eyes, blurred or tunnel vision (not including near or far-sightedness), itchy ears, earaches, ear infections, drainage from ear, ringing in ears, hearing loss, stuffy nose, sinus problems, hay fever, sneezing attacks, excessive mucus formation, chronic coughing, gagging, need to clear throat, sore throat, hoarseness, loss of voice, swollen or discolored tongue, gums or lips, canker sores, acne, hives, rashes, dry skin, hair loss, flushing, hot flashes, excessive sweating, irregular or skipped heartbeat, rapid or pounding heartbeat, chest pain, chest congestion, asthma, bronchitis, shortness of breath, difficulty breathing, bloated feeling, nausea, vomiting, diarrhea, constipation, belching, passing gas, heartburn, intestinal/stomach pain, pain or aches in joints, arthritis, stiffness or limitation of movement, pain or aches in muscles, feeling of weakness or tiredness, binge eating/drinking, craving certain foods, excessive weight, compulsive eating, water retention, underweight, fatigue, sluggishness, apathy, lethargy, hyperactivity, restlessness, poor memory, confusion, poor comprehension, poor concentration, poor physical coordination, difficulty in making decisions, stuttering or stammering, slurred speech, learning disabilities, poor physical coordination or clumsiness, numbness or tingling in hands or feet, mood swings, anxiety, fear or nervousness, anger, irritability or aggressiveness, sadness or depression, frequent illness such as colds, frequent or urgent urination, genital itch or discharge, decreased libido and PMS. Phenotypic information can be collected all in a single session, in several sessions involving a small number of questions at each session, and over weeks, months or years, creating a 'longitudinal' view of the subject's phenotype. Each of these can be a biological condition.

Functional categories also include categories that may contribute to more general categories, such as wellness, stress, anxiety, allergies, autoimmune condition, leaky gut, insulin resistance, metabolic syndrome, metabolic type, insomnia and, skin conditions.

Typically, determining the presence or absence of a condition and/or degree of the condition, also requires microbiome information for the individual, but in some cases phenotype information may be sufficient to determine presence or absence and/or degree of a biological condition in the individual. In these cases, to determine presence or absence of the condition, the phenotype score for the biological condition may be compared to a threshold value, and if the phenotype score is above the threshold value, or above or equal to the threshold value (or below the threshold value or below or equal to the threshold value, depending on the biological condition), then the biological condition is present, if not, it is not. Additionally, or alternatively, the biological condition may be assessed by assigning a degree to the condition, depending on the total phenotype score for the condition. Any suitable method of assigning degree may be used, such as quartiles, quintiles, percentage, and the like.

B. Transcriptomic Information

Data can include information about microbes in the subject's microbiome, e.g., gut microbiome or from the subject's blood transcriptome. To the extent the data includes information from a plurality of different organisms in the microbiome, the data can be classified as meta-data, such as meta-genomic, meta-transcriptomic, meta-metabolomic, meta-proteomic and meta-epigenetic.

Data can also include phenotypic information about a subject, that is, information about objectively and/or subjectively measurable traits for a subject. Data can include lifestyle information about a subject including, for example, diet, exercise, stress, alcohol use, drug use, supplement use, and sleep patterns. Data also can include biomic, e.g., environmental, information about a subject including, for example, exposure to toxins, climate, external temperature, social interactions, location, work environment, hydration, activity level, and the like.

Methods and compositions herein can utilize microbiome information for an individual. Any suitable method of determining microbiome information for the individual may be used.

Microbiome can include gut, skin, mouth, nasal, vaginal and other microbial populations associated with an individual. In certain embodiments, information regarding the gut microbiome is used. A microbiome generally comprises heterogeneous microbial populations. Microbial communities are often made up of mixed populations of organisms, including unknown species in unknown abundances. Microbial components of the microbiome can include bacteria, archaebacteria, viruses, fungi, and protists. In some cases, information regarding one, two, three, four, or all of bacteria, archaebacteria, viruses, fungi, and protists can be used. In some cases, information regarding bacteria and viruses is used.

Microbiome information can be obtained in any suitable way, typically by analysis of one or more samples from the individual. Depending on the microbial populations of interest, any suitable sample or samples may be used. Exemplary samples include earwax, sweat, breast milk, hair, blood, bile, cerebrospinal fluid, lymphatic fluid, semen, vaginal discharge, menstrual fluid, feces (stool), sputum, urine, saliva, secretions from open wounds, secretions from the eye, skin tissue (e.g., a skin biopsy), subcutaneous tissue, muscle tissue, adipose tissue, and a combination thereof. Furthermore, a sample may be obtained from, for example, the gut, the vagina, the penis, a testicle, the cervix, the respiratory system, the ear, the skin, the rectum, the kidney, the liver, the spleen, the lung, the pancreas, the small intestine, the gallbladder, the lymph nodes, the colon, a nasal passage, the central nervous system, an oral cavity, a sinus, a nostril, the urogenital tract, an udder, an auditory canal, a breast, an open wound, the eye, fat, muscle, and combinations thereof. In certain embodiments, one or more stool samples from the individual is used to determine microbiome information for the individual.

Microbiome information useful in the methods and compositions discussed herein includes information regarding microbial taxa, such as genera, species and/or strains of the microbiome, e.g., gut microbiome as determined from one or more samples such as one or more fecal samples, such as species identities and/or quantities and/or relative quantities. Microbial information can also include expression information for various genes, indicating levels of transcription of various genes of the microbial species. Microbial information can also include biochemical information, such as information regarding small molecules produced by the microbial species of the microbiome.

1. Information from Nucleic Acids

Polynucleotides can be extracted directly from the sample, or cells in the sample can first be lysed to release their polynucleotides. In one method, lysing cells comprises bead beating (e.g., with zirconium beads). In another method, ultrasonic lysis is used. Such a step may not be necessary for isolating cell-free nucleic acids.

Nucleic acids can be isolated from the sample by any means known in the art. Polynucleotides can be isolated from a sample by contacting the sample with a solid support comprising moieties that bind nucleic acids, e.g., a silica surface. For example, the solid support can be a column comprising silica or can comprise paramagnetic silica beads. After capturing nucleic acids in a sample, the beads can be immobilized with a magnet and impurities removed. In another method, nucleic acids can be isolated using cellulose or polyethylene glycol.

If the target polynucleotide is RNA, the sample can be exposed to an agent that degrades DNA, for example, a DNase. Commercially available DNase preparations include, for example, DNase I (Sigma-Aldrich), Turbo DNA-free (ThermoFisher) or RNase-Free DNase (Qiagen). Also, a Qiagen RNeasy kit can be used to purify RNA.

Alternatively, or in addition, a sample comprising DNA and RNA can be exposed to a low pH, for example, pH below pH 5, below pH 4 or below pH 3. At such pH, DNA is more subject to degradation than RNA.

If the target polynucleotide is RNA, the sample can be reverse transcribed into DNA. Reverse transcription generally takes place after a sample has been depleted of DNA.

In some aspects, a sample can be depleted of nucleic acids and nucleic acid species that are abundant relative to other nucleic acids in the sample. Some of the abundant nucleic acids may not be target nucleic acids (e.g., they may not encode sequence signatures or may not be informative of desired taxonomic information). The presence of these abundant nucleic acids can reduce the sensitivity of some of the methods described herein. This can be true, for example, if target or informative nucleic acids are rare relative to the abundant nucleic acids. Therefore, it can be advantageous to enrich a sample for target sequences by removing non-informative abundant sequences. Examples of sequences that can be removed include microbial ribosomal RNA, including 16S rRNA, 5S rRNA, and 23S rRNA. Other examples of sequences that can be removed include host RNA. Examples include host rRNA, such as 18S rRNA, 5S rRNA, and 28S rRNA.

As used herein, the term "non-informative RNA" refers to a form of non-target or non-analyte species of RNA. Non-informative RNA species can include one or more of: human ribosomal RNA (rRNA), human transfer RNA (tRNA), microbial rRNA, and microbial tRNA. Non-informative RNA species can further comprise one or more of the most abundant mRNA species in a sample, for example, hemoglobin and myoglobin in a blood sample.

Methods of enriching nucleic acid samples include the use of oligonucleotide probes. Such probes can be used for either positive selection or negative selection. Such methods often reduce the amount of non-target nucleotides.

If the target polynucleotide is DNA, then DNA can be isolated with silica, cellulose, or other types of surfaces, e.g., Ampure SPRI beads. Kits for such procedures are commercially available from, e.g., Promega (Madison, WI) or Qiagen (Venlo, Netherlands).

The isolated nucleic acids are generally sequenced for subsequent analysis. The methods described herein generally employ high throughput sequencing methods. As used herein, the term "high throughput sequencing" refers to the simultaneous or near simultaneous sequencing of thousands of nucleic acid molecules. High throughput sequencing is sometimes referred to as "next generation sequencing" or "massively parallel sequencing." Platforms for high throughput sequencing include, without limitation, massively parallel signature sequencing (MPSS), Polony sequencing, 454 pyrosequencing, Illumina (Solexa) sequencing, SOLiD sequencing, Ion Torrent semiconductor sequencing, DNA nanoball sequencing, Heliscope single molecule sequencing, single molecule real time (SMRT) sequencing (PacBio), and nanopore DNA sequencing (e.g., Oxford Nanopore).

2. Transcriptome Sequence Preprocessing

Also provided herein are methods of analyzing RNA transcripts in a heterogeneous microbial sample. The RNA transcripts can be part of a transcriptome for a cell or cells in the heterogeneous microbial sample. Information regarding the transcriptomes of a plurality of cells from different species may be obtained. The methods generally include isolating and sequencing the RNA found in a sample as described above.

The sequences obtained from these methods can be preprocessed prior to analysis. If the methods include sequencing a transcriptome, the transcriptome can be preprocessed prior to analysis. In one method, sequence reads for which there is paired end sequence data are selected. Alternatively, or in addition, sequence reads that align to a reference genome of the host are removed from the collection. This produces a set of host-free transcriptome sequences. Alternatively, or in addition, sequence reads that encode non-target nucleotides can be removed prior to analysis. As described above, non-target nucleotides include those that are over-represented in a sample or non-informative of taxonomic information. Removing sequence reads that encode such non-target nucleotides can improve performance of the systems, methods, and databases described herein by limiting the sequence signature database to open reading frames can the size of the database, the amount of memory required to run the sequence signature generation analysis, the number of CPU cycles required to run the sequence signature generation analysis, the amount of storage required to store the database, the amount of time needed to compare sample sequences to the database, the number of alignments that must be performed to identify sequence signatures in a sample, the amount of memory required to run the sequence signature sample analysis, the number of CPU cycles required to run the sequence signature sample analysis, etc.

In certain embodiments, quantitative measures of gene activity and microbial taxa are determined using the transcriptome of a microbiome of the subject. The transcript on includes RNA that is transcribed from cells in a sample, in particular, microbial cells. In certain embodiments transcriptome analyzed comprises or consists essentially of messenger RNA, in particular, microbial mRNA. In certain embodiments non-informative RNA is removed from the transcriptome before analysis. In particular, ribosomal RNA can be removed from the transcriptome. Accordingly, taxonomic analysis can be performed on mRNA rather than rRNA.

3. Taxonomic Identification

A) Paired End Alignment

To determine the identity of one or more organisms present in a sample at a specific taxonomic level, paired-end (or optionally single) transcriptome reads from that sample are aligned to the library of taxonomic signatures as described herein at that specific taxonomic level. Sequences can be aligned using, for example, the BWA aligner with the mem algorithm. (Li H. (2013) "Aligning sequence reads, clone sequences and assembly contigs with BWA-," arXiv: 1303.3997v1 [q-bio.GN].) BWA is often run with a minimal seed alignment length of 30 nt, but other BWA parameters such as the mis-match penalty can be modulated, as can downstream filters. Global thresholds for sensitivity and specificity can be tuned at this level by modulating the BWA parameters during model training after taxonomic signature generation on test data sets of known composition. These values can then be applied during the identification step. The best unique alignment of a read or read pair to a unique genome signature at a specific taxonomic level identifies that taxonomic member as being present. Some organisms will be identified to the strain taxonomic level while others may only be identified to the genus level (or higher) depending on the nature of distinct sequences available in the database to make an accurate determination. In some aspects, a microorganism or a taxon is identified as being present in the sample if at least 1, 2, 3, 4, 5, 6, 7, 8, 9, 10, 15, 20, 25, 30, 35, 40, 45, 50, 60, 70, 80, 90, 100 or more sequence signatures corresponding to the taxon are detected in the sample. In some aspects, a microorganism or a taxon is identified as being present in the sample if at least 1, 2, 3, 4, 5, 6, 7, 8, 9, 10, 15, 20, 25, 30, 35, 40, 45, 50, 60, 70, 80, 90, 100 or more sequence reads are detected for a sequence signature in the sample. In some aspects, a read is determined to match a sequence signature if the read is at least 90%, 95%, 96%, 97%, 98%, 99%, 99.5%, 99.9% or 100% identical to at least a portion of the sequence signature or the entire sequence signature. In some aspects, a read is determined to match a sequence signature if the sequence signature is at least 90%, 95%, 96%, 97%, 98%, 99%, 99.5%, 99.9% or 100% identical to at least a portion of the read or the entire read. In a preferred embodiment, calling or identifying a microorganism as being present at one or more taxonomic levels requires at least 25 reads of at least 100 nucleotide and a mismatch rate no greater than 2% when aligned against the curated database/library of unique genome signatures.

Alternatively, or in addition, the methods, systems and databases herein can be used to identify a biochemical activity present in the sample. In some embodiments, the methods include aligning sequencing reads to a database comprising open reading frame information that is associated with a particular biological, e.g., biochemical, activity or pathway, as described above. Some of such methods can include identifying taxonomic information for a sequence. Examples include the GOTTCHA algorithm, which detects sequence signatures that identify nucleic acids as originating from organisms at various taxonomic levels. Nucleic Acids Res. 2015 May 26; 43 (10): e69. Other methods include MetaPhlAn, Bowtie2, mOTUs, Kraken, and BLAST. Some of such methods do not include identifying taxonomic information for the sequence, but instead may identify the biological activity, pathway, protein, functional RNA, product, or metabolite associated with a particular sequence read or sequence signature.

b) Use of Flanking Sequences

In another embodiment, transcriptome sequences that align to one portion of the unique genome signature database/library but do not align to sequences flanking the first portion in that alignment are eliminated.

In one version of this embodiment, identification of organisms on a particular taxonomic member at a taxonomic level can be determined by making use of sequences that flank sequences in the taxonomic signature. That is, the method can make use of sequences of the genome removed from the genome in the generation of the taxonomic signature. In this method transcriptome sequences are often first aligned to the taxonomic signature sequences. Then, portions of the aligned transcriptome sequences that do not, themselves, align with the signature sequences can be compared to the sequences that flank the signature sequences. If there is insufficient homology between these flanking sequences, the entire sequence read can be removed from the alignment protocol. The minimum level of homology required for a sequence to remain in alignment can be, for example, at least 90%, at least 95%, at least 98%, at least 99% or 100%.

c) Microorganism Quantitation

The methods, systems, and databases described herein can also be used to quantify a characteristic in a heterogeneous sample. In one aspect, provided herein are methods for quantifying microorganisms in a sample. Alternatively, or in addition, provided herein are methods for quantifying a particular biochemical activity associated with a heterogeneous microbial sample or a microorganism contained therein. Transcriptome sequences from the sample can be mapped to the ORF library described above. In some aspects, ORF library can be used to infer taxonomic information about the organisms present in the sample. Alternatively, or in addition, sequences that map to the library can be annotated to indicate information such as gene identity and gene function.

Quantification of abundance can be done by computer by summing up the non-overlapping length of profiles found for a taxonomic member (Linear Length or L), then determining the read coverage across that length (Linear Depth of Coverage or DOC). In some aspects, the non-overlapping length is or comprises a sequence signature informative of taxonomic information.

Normalizing over the sum of all DOCs for a specific taxonomic level allows one to arrive at the relative abundance (RA) of that taxonomic member. In one embodiment, normalization comprises: determining the number of base pairs contained in a particular ORF, determining an average depth of coverage for the entire length of the ORF using the number nucleotides contained in sequence reads corresponding to the ORF and the length of the ORF, and determining the proportion of all sequence reads that correspond to the ORF.

Normalization can comprise determining an average depth of coverage for ORFs identified in the sequencing data, summing the averages to generate a total depth of coverage, and dividing the depth of coverage for an ORF of interest by the total depth of coverage. Such a method can be used to determine a relative amount or proportion of sequence reads for the target ORF in the sequencing data. Such methods can also account for the relative differences in lengths of ORFs, allowing for more direct comparisons, because the methods can use the depth of coverage for an ORF rather than the total number of bases read. Thus, a number of base reads in a 1,000 bp ORF would have half the total depth of coverage compared to the same number of base reads in a 500 bp ORF. The relative amount or proportion of the ORF in the sample can be used to infer the relative activity of the target ORF.

In some aspects, the amount or relative amount can be compared to a reference value. Examples of a reference value include a normal value and a cutoff value that is a specified distance from a normal value (e.g., in units of standard deviation). The reference value may be determined from a different sample from the same subject (e.g., when the subject was known to be healthy or prior to administration of the food, supplement, or medication). The reference value may also be determined from one or more samples from other healthy subjects. The reference value may be an absolute or relative value. The reference value for different biological conditions may be different for the same microbial entity, e.g., species.

The measure of gene expression at each taxonomic level can be calculated based on the Reads Per Kilobase (RPK) of transcript per Million mapped reads. Additional filters can be applied at this step on read count, L, DOC, or RA with thresholds determined during the model training step. Note this relative abundance will be for the DNA or RNA fraction of that taxonomic member in the sample at time of library prep. If the source was RNA, then the relative abundance calculated can correspond to the relative activity of that organism in the sample (e.g., gene expression levels). Alternatively, or in addition, if the source was RNA, then the relative abundance calculated for an ORF can correspond to the relative activity of that ORF, including the activity or pathway. If the source was DNA, one relates to relative abundance of that organism assuming a single genome copy per organism. The taxonomic relative activity can be quantified by finding the median or mode of non-zero Reads Per Kilobase (RPK) of transcript per Million mapped reads (RPKM values) and inversing scaling by the fraction of active genes.

The output of this process can be a report that indicates for a subject sample the taxa of microorganisms in the sample. If the taxonomic identity of the sample cannot be identified at a particular taxonomic level the report can indicate the intensity at the next highest taxonomic level. The report can also indicate quantitative information about the sample this can include, for example, the relative amounts of different microorganisms in the sample. It can also indicate relative activity of microorganisms in the sample based on relative gene expression. This can include, for example, types of genes that are either expressed in high amounts or alternatively, in low amounts. Alternatively, or in addition, the report can indicate the identity and relative amounts of biochemical activities in the sample. The report can indicate changes as to biochemical activity in the sample over time, such as during a time course. The report can indicate differences between samples, including samples collected from the same source at different times. The source can be a subject, including a human subject.

In some aspects, limiting the sequence signature database to open reading frames can reduce the size of the database, the amount of memory required to run the sequence signature generation analysis, the number of CPU cycles required to run the sequence signature generation analysis, the amount of storage required to store the database, the amount of time needed to compare sample sequences to the database, the number of alignments that must be performed to identify sequence signatures in a sample, the amount of memory required to run the sequence signature sample analysis, the number of CPU cycles required to run the sequence signature sample analysis, etc.

Reports can sometimes be output to paper, a screen, or a database. Reports can also be stored for later analysis or viewing. Reports can be sent to third parties, such as subjects, healthcare professionals, customers, collaborators, etc.

As part of assessing the microbiome, one or more biochemical activities may be assessed. The assessment may include one or more of quantifying an enzymatic activity assay, a growth-inhibition culture, metabolic profiling, quantifying one or more biochemical molecules, or any combination thereof. Of particular interest are short chain fatty acids, for example butyrate and propionate. In certain embodiments, levels of butyrate are assessed and included in the microbiome information.

In certain embodiments a microbiome score for a biological condition, similar to a phenotype score, is assigned to the individual. The score may be obtained by any suitable method.

Typically, determining the presence or absence of a condition and/or degree of the condition, also requires phenotype information for the individual, but in some cases microbiome information may be sufficient to determine presence or absence and/or degree of a biological condition in the individual. In these cases, to determine presence or absence of the condition, the microbiome score for the biological condition may be compared to a threshold value, and if the microbiome score is above the threshold value, or above or equal to the threshold value (or below the threshold value or below or equal to the threshold value, depending on the biological condition), then the biological condition is present, if not, it is not. Additionally, or alternatively, the biological condition may be assessed by assigning a degree to the condition, depending on the total microbiome score for the condition. Any suitable method of assigning degree may be used, such as quartiles, quintiles, percentage, and the like.

In certain embodiments, for a biological condition the phenotype score and the microbiome score may be combined, either with or without weighting each of the scores, to produce a combined score. Any suitable method may be used to combine the scores, such as simple addition. The combined score can then be used to determine presence or absence and/or degree of a biological condition in the individual. In these cases, to determine presence or absence of the condition, the combined score for the biological condition may be compared to a threshold value, and if the combined score is above the threshold value, or above or equal to the threshold value (or below the threshold value or below or equal to the threshold value, depending on the biological condition), then the biological condition is present, if not, it is not. Additionally, or alternatively, the biological condition may be assessed by assigning a degree to the condition, depending on the total combined score for the condition. Any suitable method of assigning degree may be used, such as quartiles, quintiles, percentage, and the like.

4. Gene Activity Quantitation

The methods, systems and databases herein can be used to identify activity of a gene or a biochemical pathway present in the sample. In some embodiments, the methods include aligning sequencing reads to a database comprising open reading frame information that is associated with a particular biochemical activity or pathway, as described above. Some of such methods can include identifying taxonomic information for a sequence. Examples include the VIOMEGA algorithm (see WO 2018/160899 (Vuyisich et al.) or GOTTCHA algorithm, which detects sequence signatures that identify nucleic acids as originating from organisms at various taxonomic levels. Nucleic Acids Res. 2015 May 26; 43 (10): e69. Other methods include MetaPhlAn, Bowtie2, mOTUs, Kraken, and BLAST. Some of such methods do not include identifying taxonomic information for the sequence, but instead may identify the biochemical activity, pathway, protein, functional RNA, product, or metabolite associated with a particular sequence read or sequence signature.

"Gene activity" or "activity of a gene" is a generally a function of transcription, e.g., the quantity of RNA in a sample encoding the gene. This can be done at any taxonomic level. For example, gene activity could be a measure of activity of the gene in a single species, or it could be activity of the gene across organisms belonging to a common genus, class, order or phylum. The term "gene" can refer to orthologs of a gene across different species. Such orthologs can be identified, for example, with the KEGG or theology.

C. Functional Activities And Functional Activity Scores

Functional activities are biological activity categories including biological or health functions or conditions at the cellular, organ or organismal level. Functional activities are assigned functional activity scores based on such data. Functional activity scores represent quantitative measures of functional activity. A functional category can involve any function related to health or wellness. Functional categories can embrace health parameters, health indicators, health conditions and health risks. The activity of the function is assessed by analyzing -omic, e.g., transcriptomic data, which is collected from active, living organisms, e.g., expressing RNA from their genomes.

Functional activity includes integrative functional activities and non-integrative functional activities. Nonintegrative functional activities are based on a single type of data or function, such as microbiome pathway activity data, taxa group activity data and host transcriptomic data. Integrative functional activities are based on an be based on a plurality of different kinds of data or functions. For example, such functional activities can combine pathway activity data in taxa activity data.

A) Pathways

In certain embodiments, functional activities include the activities of one or more pathways. As used herein, the term "pathways" refers to biological pathways, which are sequences of proven molecular events (such as enzymatic reactions or signal transduction or transport of substances or morphological structure changes) that lead to specific functional outcomes (such as secretion of substances, sporulation, biofilm formation, motility). Many biological pathways are known in the art, and examples can be found on the web at wikipathways.org/index.php/WikiPathways, pathwaycommons.org, and proteinlounge.com/Pathway/Pathways.aspx. Manual expert curation of scientific literature also can be used to reconstruct or create custom biological pathways. Biological pathways can include a number of genes that encode peptides or proteins, which play specific signaling, metabolic, structural or other biochemical roles in order to carry out various molecular pathways.

As used herein, the terms "biochemical activity" and "biochemical pathway activity" refer to activity of a biochemical pathway. Pathways of interest include, without limitation, butyrate production pathways, LPS biosynthesis pathways, methane gas production pathways, sulfide gas production pathways, flagellar assembly pathways, ammonia production pathways, putrescine production pathways, oxalate metabolism pathways, uric acid production pathways, salt stress pathways, biofilm chemotaxis in virulence pathways, TMA production pathways, primary bile acid pathways, secondary bile acid pathways, acetate pathways, propionate pathways, branched chain amino acid pathways, long chain fatty acid metabolism pathways, long chain carbohydrate metabolic pathways, cadaverine production pathways, tryptophan pathways, starch metabolism pathways, fucose metabolism pathways.

B) Taxa Groups

In certain embodiments, functional activities include the activities of one or more taxa groups. Microbial taxa include taxonomic designation at any taxonomic level, e.g., species, genus, order or phylum. Active microbial taxa are taxa that are not really present but that are metabolically active, e.g., as measured by transcriptional levels of the microbial genome. Groups of microbial taxa whose activity contribute to functional activity in a functional category are referred to herein as "taxa groups". So, for example, pro-inflammatory taxa group can comprise one or more of: proteobacteria, opportunistic bacteria or pathogens, viruses; anti-inflammatory taxa group can comprise one or more of: butyrate producers, Lactobacilli and Bifidobacteria; intestinal barrier disruptors taxa comprise one or more of: Ruminococcos torques, Ruminococcus gnavus, *Serratia*, Sutterella, and other mucus-degrading or epithelial layer-disrupting organisms.

Taxa groups of interest include, without limitation, *Prevotella* (genus)/*Bacteroides* (genus) ratio, *Eubacterium rectale* (species), *Eubacterium eligens* (species), *Faecalibacterium prausnitzii* (species), *Akkermansia muciniphila* (species), metabolic-related probiotic species (functional group), *Roseburia* (genus), *Bifidobacterium* (genus), *Lactobacillus* (genus), *Clostridium butyricum* (species), *Allobaculum* (genus), *Firmicutes* (phylum)/Bacteroidetes (phylum) ratio, Lachnospiraceae (family), Enterobacteriaceae (family), *Ralstonia pickettii* (species), *Bilophila wadsworthia* (species).

2. Integrative Functional Activities

Examples of integrative functional categories include, without limitation, inflammatory activity, metabolic fitness, digestive efficiency, intestinal barrier health, protein fermentation, gas production, microbial richness, SIBO-like Pattern, detoxification potential (ability of microbiome to detoxify the body), gut neuro-balance (impact of microbiome on the brain, e.g., by production of neurotransmitters), neurological health, cardiovascular health, hormonal balance, musculoskeletal health, hepatic function, urogenital health, mitochondrial activity, immune function, gastrointestinal health, diabetes, skin conditions and infectious disease.

3. Hierarchical Functional Activities

Figure 3:
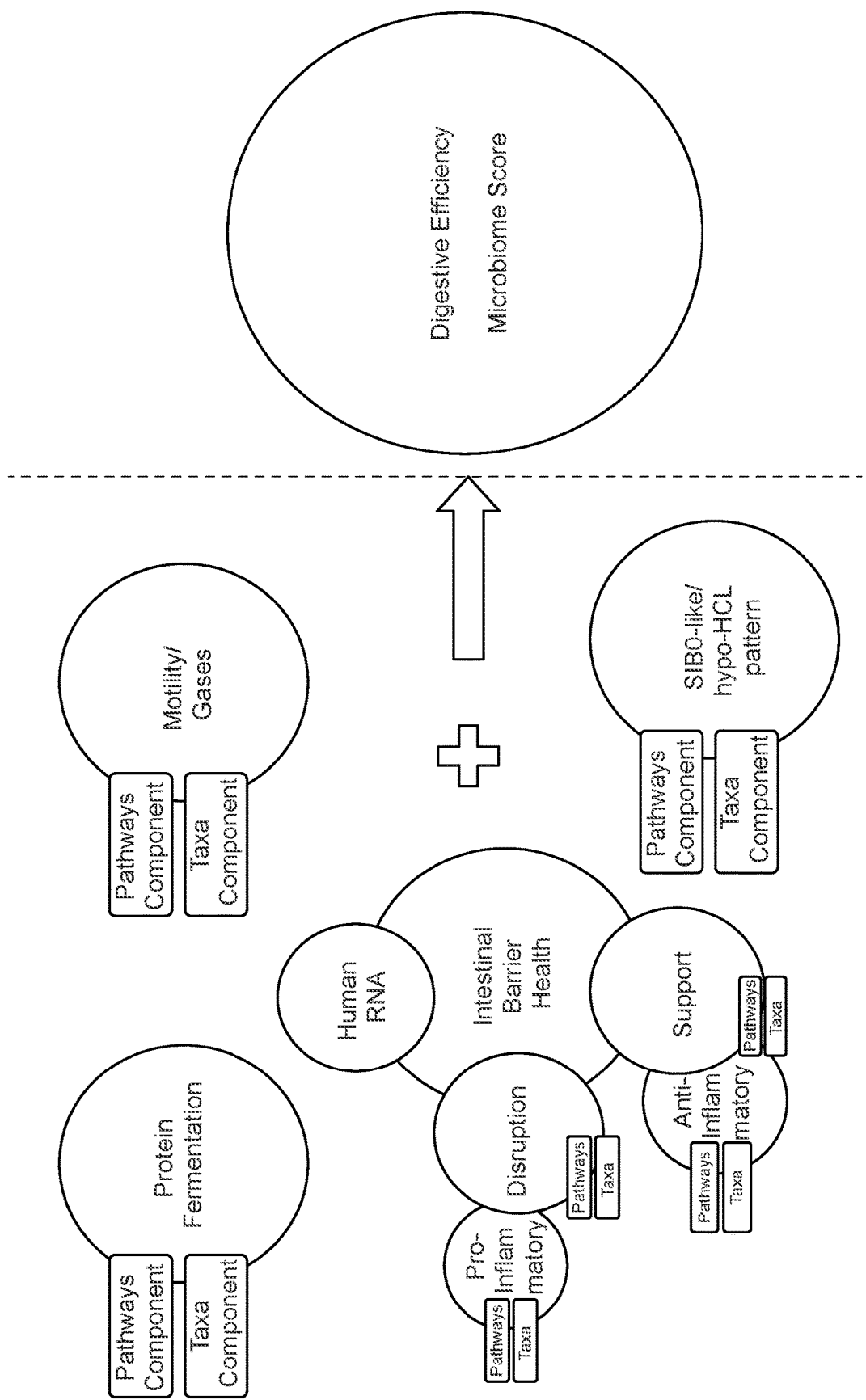
FIG. 3 shows development of a functional activity score for a high-level health metric, in this example, digestive efficiency. The functional activity is a composite of functional activity scores for a number of lower order functional categories. In this example, functional categories include protein fermentation, motility/gases, intestinal barrier health and SIBO-like/hypo-HCL pattern. Intestinal barrier health, in turn, is a composite of still further lower order functional categories including pro-inflammatory and anti-inflammatory components. In this example, scores for each of the intermediate functional categories in the hierarchy are based on both biochemical pathway activity (pathway component) and active taxa (taxa component).
Figure 4:
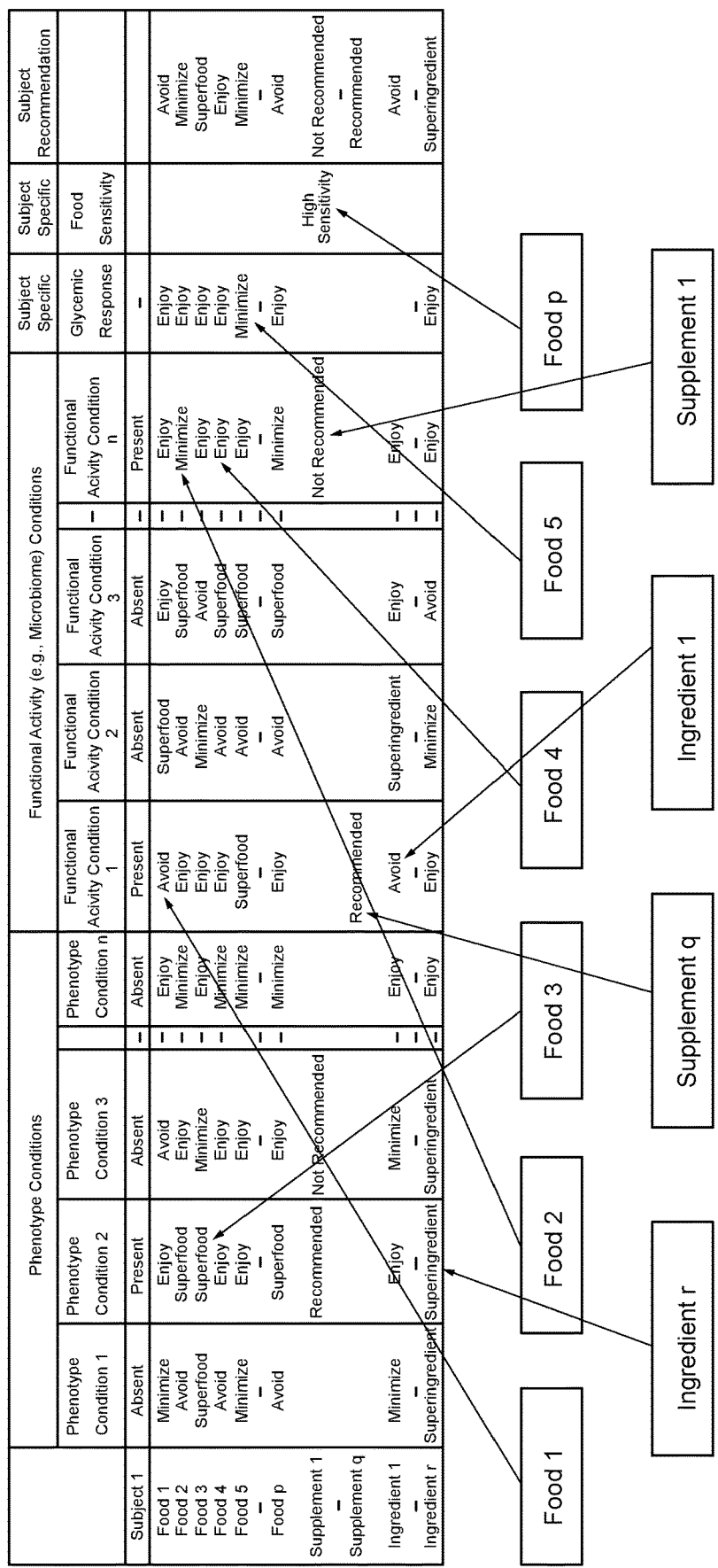
FIG. 4 shows an exemplary application of recommendation engine that applies logic as described herein to produce final recommendations for foods.

Functional categories can be hierarchical in nature, with functional categories at lower levels in the hierarchy being aggregated into functional categories at higher levels in the hierarchy. For example, at a lowest level a single biochemical pathway or a group of microbial taxa can serve as a function category. Combinations of pathways and microbial taxa groups can be integrated into higher level categories. This includes, for example, a plurality of pathways, a plurality of taxa groups or at least one pathway and at least one taxa group. Referring to FIG. 3, inflammatory activity is a functional category that aggregated pro-inflammatory and anti-inflammatory components. Each of these components represents a functional category. In turn, each of the pro-inflammatory and anti-inflammatory categories aggregated scores from biochemical pathways and taxa groups. Referring to FIG. 4, a number of functional categories can be aggregated into a higher order functional category, in this case, digestive efficiency. More specifically, in this example, digestive efficiency aggregated scores from the categories protein fermentation, motility/gases, intestinal barrier health and SIBO-like/hypochlorhydrea pattern. While the final aggregated functional category is provided with a functional activity score, each sub functional category which is comprised within the highest functional category may itself be provided with a discrete score or other logic may be used to aggregate functional activities of the subcategories into the topmost functional category.

4. Functional Activity Score

A "functional activity score" refers to a quantitative measure assigned to an activity or state of a functional activity. A functional activity score can be assigned to a functional category in a subject based on -omic data, e.g., data from the microbiome, such as meta-transcriptomic data. A functional activity score can be determined, for example, based entirely on the score for a pathway functional activity. Alternatively, where the functional activity is a composite of more than one pathway and taxa activity scores, optimality can be determined by reference to scores in a population of individuals.

A functional activity score can be given as within or outside a reference value, such as a range. The reference value can be derived from values across a population of subjects. For example, the reference range may constitute a statistical range within the population, such as a standard deviation from the mean. Alternatively, the reference range may be determined by expert analysis, by logic and/or with reference to literature sources. The value can be given as a continuous or discrete variable. For example, discrete variables can be given as "low" "medium" or "high", with "medium" constituting the reference range. Both "low" and "high" may be outside the reference range. Alternatively, the score can be given as "good", "average" or "needs improvement". A score of "needs improvement" indicates a score outside of a reference range for which action is recommended.

A functional activity score outside of a reference range can be considered suboptimal and indicative of the presence of a functional activity condition.

Quantitative measures can be given as a discrete or continuous range. Quantitative measures can be absolute numbers or relative amounts, such as normalized amounts. Quantitative measures include statistical measures such as mean, variance and standard deviation. For example, a quantitative measure can be a number, a degree, a level or bucket. A number can be a number on a scale, for example 1-10. Alternatively, the quantitative measure can embrace a range. For example, ranges can be high, medium and low; severe, moderate and mild; or actionable and non-actionable. Buckets can comprise discrete numerals, such as 1-3, 4-6 and 7-10. quantitative measure (number, range, relative amount, etc.).

IV. Food Information

A. Knowledge Database

Figure 2:
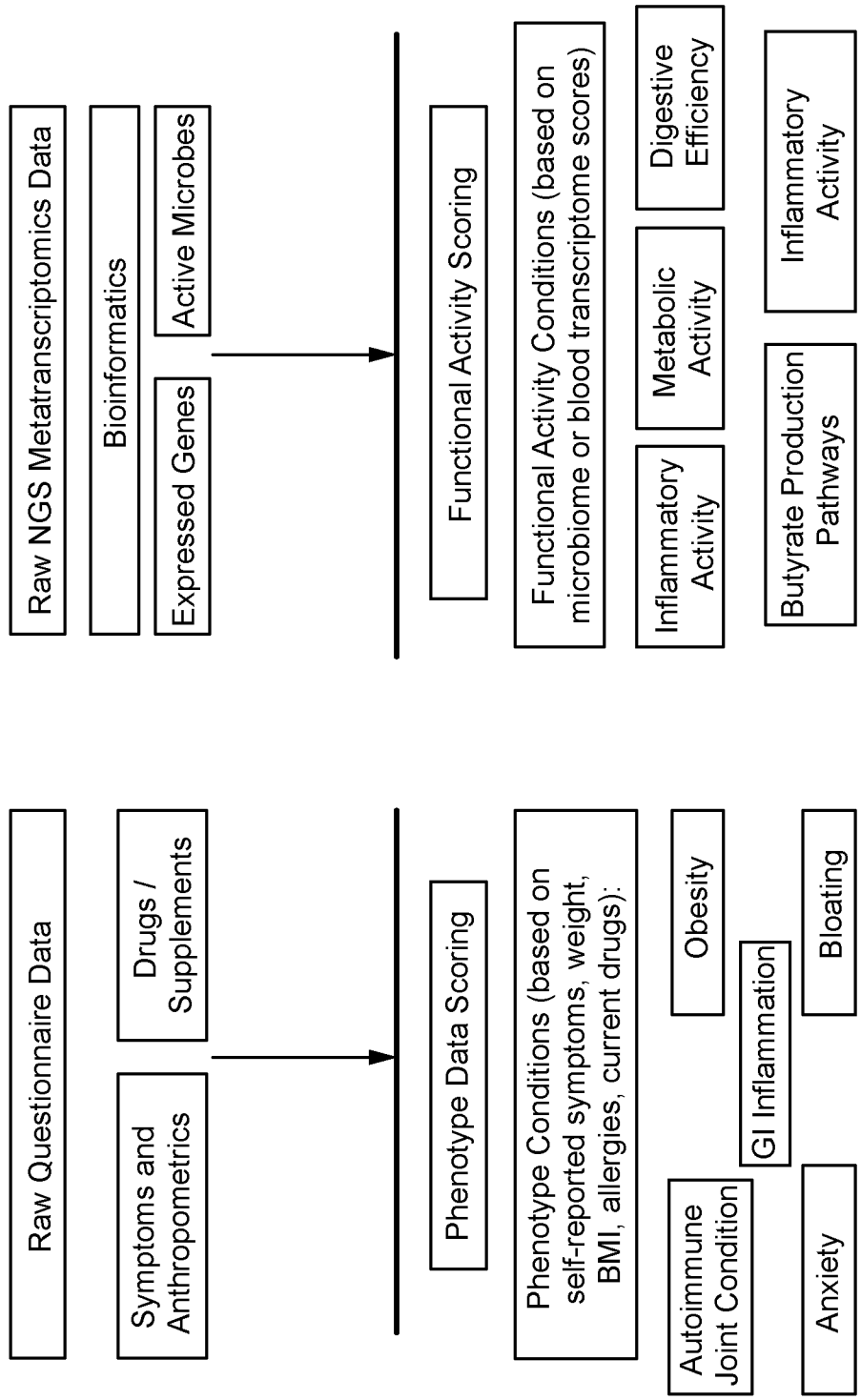
FIG. 2 shows an exemplary algorithm for determining the presence or absence of biological conditions from -omic data collected from the subject. Raw questionnaire data can include symptoms in anthropometrics and or drugs/supplements being taken by the subject. This data is subject to phenotype data scoring. Scores are used to infer the presence or absence of phenotype conditions. Raw next generation sequencing (NGS) meta-transcriptomics data is processed by bioinformatics to identify expressed genes (e.g., KO's) and active microbes. This data is subject to the functional activity scoring. Functional activity scores are used to infer the presence or absence of functional activity conditions.

A knowledge database is provided from which personalized recommendations can be made. The database includes, for each of a plurality of food items, e.g., foods, supplements and/or ingredients, an entry indicating a desirability rating of the food for particular biological conditions. The desirability rating can indicate the effect, e.g., the relative degree of harm or benefit, that consuming the food has on the biological condition. The form of the entries can be hierarchical in nature, from most beneficial to least beneficial for the condition. The entries can be in the form of recommendations on whether the food of supplement should be consumed to ameliorate the condition. There typically will be a plurality of recommendation categories, for example, at least or exactly any of 2, 3, 4, 5, 6 or 7. For example, the categories can be, from most to least beneficial, "good", "neutral" or "bad". Alternatively, the categories can be "superfood", "enjoy", "minimize" and "avoid." Alternatively, the categories can be ranked "1", "2", "3", "4" or "5" to designate least to most beneficial for a particular condition. An exemplary food recommendation database is presented in FIG. 2. Each entry (row) represents a food or micronutrient. Each column (feature) represents a biological condition (phenotype conditions and functional activity conditions). Each cell indicates the classification of the food or nutrient for the particular biological condition. In this case, foods and nutrients are classified hierarchically from most beneficial to least beneficial as one of four recommendations for the condition: "superfood", "enjoy", "minimize" and "avoid."

Foods, supplements or ingredients may be classified simply as positive, e.g., "recommended" or neutral, e.g., no recommendation given. In certain embodiments, supplements are given a positive, neutral or negative desirability rating, a positive or negative rating or a positive or neutral rating. Ingredients can be given ratings from the same hierarchical structure as foods, e.g., "super ingredient", "enjoy", "minimize" and "avoid".

Particular recommendations can be assigned by experts based on knowledge from literature about the effect of a food on a condition and on expert knowledge. Published literature in peer reviewed journals can be reviewed, prioritizing human studies with large cohorts and having sufficient confidence intervals, or having placebo groups. These types of studies can be supplemented with smaller studies with less well derived effects, or with conditions having fewer journal articles covering the association.

B. Foods, Supplements and Ingredients

The methods and compositions described herein can be used to provide food, supplement and/or ingredient recommendations to an individual. The recommendations are based on the predicted effects of the food, supplement and/or ingredient on one or more biological conditions of the individual.

To provide the recommendations, the effects of a food, supplement and/or ingredient on a plurality of conditions, e.g., at least 1, 2, 3, 4, 5, 6, 7, 8, 9, or 10 biological conditions of the individual, may be predicted and the predicted effects may be combined to produce an overall recommendation for the food, supplement or ingredient. The predicted effect corresponds to the desirability, e.g., the desirability of a food, which in turn corresponds to the recommendation for the food. For example, a food with a negative effect on a biological condition is a highly undesirable food, and a recommendation for that food could be "avoid" or "minimize," depending on the degree of the negative effect. The process may be repeated for a desired number of foods and/or supplements. The recommendations may be in the form of an indication of the desirability of intake of the food, supplement and/or ingredient. Any suitable number of levels of desirability may be designated for a food, e.g., at least 2, 3, 4, 5, or 6 levels of desirability. For example, in the case of a food, four levels of desirability may be used, such as emphasize the food in the diet (e.g., a "superfood,"), food can be eaten regularly, such as once every one or two days (e.g., "enjoy"), the food can be eaten sometimes, such as once a week (e.g., "minimize"), or don't allow the food in the diet (e.g., "avoid"). This division of levels of desirability is exemplary and any suitable number of levels may be used. For a supplement, type of supplement, which may include specific brand of supplement, and, optionally, dosing and/or timing of the supplement may be supplied.

Any desired number of foods and/or supplements may be included in the recommendations. In some cases, at least 5, 10, 15, 20, 30, 40, 50, 60, 70, 80, 90, 100, 120, 150, 200, 250, or 300 foods may be included in the recommendations, with each food having a designation of desirability for the individual, such as four levels as described above. TABLE 2 provides an exemplary listing of foods for which a designation of desirability may be given.

TABLE 2

| Exemplary Foods |
| --- |
| Abalone |
| Acacia Gum |
| Adzuki Beans |
| Agar Agar |
| Agave Nectar |
| Alfalfa Sprouts |
| Allspice |
| Almond Milk (unsweetened) |
| Almonds |
| Amaranth |
| Anchovy |
| Apple (medium, organic) |
| Apricot |
| Artichoke |
| Arugula |
| Asparagus |
| Aspartame |
| Avocado |

TABLE 2-continued

| Exemplary Foods |
|---|
| Avocado Oil |
| Bamboo Shoots |
| Banana (small) |
| Barley |
| Basil |
| Bay Leaf |
| Beans (baked or refried) |
| Bean Sprouts |
| Beef (fatty, grass-fed) |
| Beef (lean, grass-fed) |
| Beer |
| Beet |
| Beet Greens |
| Beet Sugar |
| Bell Pepper (organic) |
| Black Beans |
| Blackberry |
| Black Eyed Peas |
| Black Pepper |
| Black Tea (brewed) |
| Blueberry |
| Bok Choy |
| Bone Broth (fish) |
| Bone Broth (mammal) |
| Bone Broth (poultry) |
| Boston Beans |
| Boysenberry |
| Brazil Nuts |
| Breadfruit |
| Broccoli |
| Brown Mushrooms |
| Brown Rice |
| Brown Sugar |
| Brussels Sprouts |
| Buckwheat |
| Buffalo |
| Bulgur |
| Burdock Root |
| Butter |
| Cabbage |
| Cane Sugar |
| Canned Vegetables |
| Canola Oil |
| Capers |
| Caraway Seed |
| Cardamom |
| Cardoon (thistle stem) |
| Carob |
| Carrot |
| Cashews |
| Cassava |
| Catfish |
| Cauliflower |
| Caviar or Roe |
| Cayenne Pepper |
| Celeriac |
| Celery (organic) |
| Celery Seed |
| Chanterelle Mushrooms |
| Chard |
| Cheese |
| Cherry (organic) |
| Chervil |
| Chestnuts |
| Chia Seeds |
| Chicken (dark) |
| Chicken (white) |
| Chickpeas |
| Chicory (root) |
| Chili Powder |
| Chlorella |
| Cilantro |
| Cinnamon |
| Cloves |
| Cocoa (unsweetened) |
| Coconut MCT Oil |
| Coconut Meat |
| Coconut Milk (unsweetened) |

TABLE 2-continued

| Exemplary Foods |
|---|
| Coconut Oil |
| Coconut Water |
| Cod, Alaskan |
| Coffee (brewed, organic) |
| Collard Greens |
| Coriander |
| Cornish Game Hen |
| Corn Syrup |
| Corn Tortilla (organic, non-GMO) |
| Couscous |
| Cranberry |
| Crayfish |
| Cucumber |
| Cumin |
| Cured Meat |
| Currant |
| Curry Powder |
| Daikon |
| Dandelion Greens |
| Dates |
| Dextrose |
| Dill (fresh) |
| Duck |
| Dungeness Crab, Pacific |
| Eel |
| Egg (large) |
| Eggplant |
| Egg White |
| Egg Yolk |
| Elderberry |
| Emu |
| Endive |
| Enoki Mushrooms |
| Escarole |
| Farro |
| Fava Beans |
| Fennel Bulb |
| Fennel Seed |
| Fenugreek Seed |
| Fermented Vegetables |
| Fiddlehead Ferns |
| Fig |
| Filberts |
| Filberts or Hazelnuts |
| Flax Oil |
| Flax Seeds |
| Flounder |
| Freekeh |
| French Fries |
| Fruit Juices |
| Game Meat (venison, elk) |
| Garlic |
| Ghee |
| Ginger |
| Goat |
| Goat Cheese |
| Goat Milk |
| Goji Berry |
| Goose |
| Gooseberry |
| Gourd |
| Granola Bars |
| Grapefruit |
| Grape Leaves |
| Grape Seed Oil |
| Grapes (organic) |
| Green Beans |
| Green Tea (brewed) |
| Guava |
| Haddock |
| Halibut, Pacific |
| Hard Squash |
| Heavy Cream (33% fat) |
| Hemp Hearts |
| Herbal Tea (brewed) |
| Herring |
| Hickory Nuts |
| Honey |

TABLE 2-continued

Exemplary Foods

Horseradish
Hot Pepper (organic)
Huckleberry
Hydrogenated Vegetable Oil
Iodized Salt
Jackfruit
Jerusalem Artichoke
Jicama
Kale
Kamut
Kasha
Kefir
Kimchi
Kiwi
Kohlrabi
Kombucha
Kumquat
Lamb
Lard
Leek
Lemon
Lentils
Lettuce
Lima Beans
Lime
Lobster
Loganberries
Lo Han
Lotus Seeds
Lychee
Maca
Macadamia Nuts
Mace
Mackerel
Maitake Mushrooms
Maltose
Mango
Mangosteen
Manuka Honey
Maple Syrup
Margarine
Marionberry
Marjoram
Melon
Millet
Miso
Molasses
Morel Mushrooms
Mulberries
Mushrooms
Mussel
Mustard Greens
Mustard Seed
Natto
Nectarine (organic)
Nutmeg
Oatmeal (flavored)
Oats
Octopus
Okra
Olive Oil
Olives
Onion
Orange
Oregano
Ostrich
Oyster Mushrooms
Papaya
Paprika
Parsley
Parsnip
Passionfruit
Peach
Peanuts
Pear (organic)
Peas
Pecans
Peppermint (fresh)

TABLE 2-continued

Exemplary Foods

Perch
Persimmon
Pheasant
Pickle (unsweetened)
Pineapple
Pine Nuts
Pinto Beans
Pistachios
Plantain
Plum
Pomegranate
Poppy Seed
Pork (lean)
Portabella Mushrooms
Potato (small, organic)
Processed Cheese
Processed Meat
Prunes
Pummelo
Pumpkin
Pumpkin Seeds
Quail
Quinoa
Radicchio
Radish
Rainbow Trout
Raisins
Raspberry
Red Beans
Red/Green/Romaine Lettuce
Rhubarb
Rice Cakes (flavored)
Rice Milk
Rice Noodles
Ricotta or Cottage Cheese (2% fat)
Rosemary (fresh)
Rutabaga
Rye (sprouted bread)
Saccharin
Safflower Oil
Saffron
Sage
Salmonberry
Salmon, Pacific (wild-caught)
Sardine
Sauerkraut
Savoury
Scallops
Scrod
Sea Salt or Himalayan Salt
Seaweed (fresh)
Sesame Seeds
Sheep Cheese
Sheep Milk
Shellfish Clam
Shellfish Oyster
Shitake Mushrooms
Shortening
Shrimp (domestic)
Snap Peas
Soda (regular or diet)
Sole
Sour Cherries
Sour Cream
Soybeans (non-GMO)
Soy Milk (unsweetened)
Spearmint (fresh)
Spinach (organic)
Spirulina
Sprouted Radish
Seeds
Squid
Star Fruit
Stevia
Strawberry (organic)
Straw Mushrooms
Sucralose
Sugar (white)

TABLE 2-continued

| Exemplary Foods |
| --- |
| Summer Squash |
| Sunflower Seeds |
| Sweet Potato/Yam |
| Swiss Chard |
| Tapioca |
| Taro |
| Tarragon |
| Tempeh |
| Thyme |
| Tilapia |
| Tofu |
| Tomato (organic) |
| Triticale |
| Tuna (pole caught) |
| Turbot |
| Turkey (dark) |
| Turkey (white) |
| Turmeric |
| Turnip |
| Vanilla Extract |
| Veal |
| Vinegar |
| Vinegar Apple Cider |
| Walnuts |
| Water Chestnuts |
| Watercress |
| Wheatgrass |
| Wheat (sprouted bread) |
| Whey |
| White Beans |
| White Flour |
| White Rice |
| White Tea (brewed) |
| Whole Milk |
| Wild Rice |
| Wine |
| Xanthan Gum |
| Xylitol |
| Yam or Sweet Potato |
| Yeast |
| Yogurt (flavored) |
| Yogurt (plain) |
| Zucchini Squash |

Alternatively, or additionally, one or more supplements may be recommended for the individual. In the case of supplements, at least 1, 2, 3, 4, 5, 6, 7, 8, 9, 10, 11, 12, 13, 14, 15, 16, 17, 18, 19, or 20 supplements may be recommended. For supplement recommendations, microbiome features are considered, and the presence or absence of certain microbes, and in some cases relative abundances or other microbiome information, is used to determine supplement recommendations. TABLE 3 provides an exemplary listing of supplements, some or all of which may be recommended.

TABLE 3

| Exemplary Supplements | |
| --- | --- |
| Supplement | Category |
| ABx Support | Probiotics |
| Atrantil | Digestive Support |
| Berberine | Polyphenols |
| BioPro | Probiotics |
| Cal-Mag Butyrate | Gut Support |
| Digestive Enzymes Ultra with Betaine HCl | Digestive Enzyme |
| Formula 20 | Digestive Enzyme |
| Gastrus | Probiotics |
| GI Revive | Digestive Support |
| Glutathione-SR | Antioxidant |
| Iberogast | Prokinetic |

TABLE 3-continued

| Exemplary Supplements | |
| --- | --- |
| Supplement | Category |
| Klean Probiotic | Probiotics |
| Lactoprime Plus | Probiotics |
| Meriva 500-SF | Polyphenols |
| Ortho Biotic | Probiotics |
| PaleoFiber | Prebiotic |
| Panplex 2 Phase | Digestive Enzyme |
| PhytoGanix | Polyphenols |
| Polyresveratrol SR | Polyphenols |
| Pomegranate Plus | Polyphenols |
| Prebiotic Powder | Prebiotic |
| Pro 15 | Probiotics |
| Resveratrol Supreme | Polyphenols |
| Spectra Reds | Polyphenols |
| Theracurmin HP | Polyphenols |
| Theraflavone | Polyphenols |
| Therbiotic Complete | Probiotics |
| Therbiotic Factor 6 | Probiotics |
| Ultraflora Spectrum | Probiotics |
| Vital 10 | Probiotics |
| VSL 3 Pouch | Probiotics |

Ingredients are components of food or supplements. They include, for example:

Probiotics (each subject can get specific strains or species recommended, and some subjects may not get a probiotic recommendation): *B. Infantis, S. thermophilus, Lactobacillus curvatus, L. paracasei, L. plantarum, L. delbrueckii* subsp. *Bulgaricus, Lactobacillus gasseri, L. amylovorus* (LA), *L. fermentum, Lactobacillus rhamnosus;*

Prebiotics (each subject can get specific types of oligosaccharides, and some subjects may not get a prebiotic recommendation at all): FOS, Inulin, Resistant Starch, Arabinan, PHGG;

Foods/herbs/seeds and or some of their extracts: African Mango, Aloe Vera Leaf Gel, American *Ginseng*, Berberine, *Gymnemma sylvestre*, Fenugreek, Milk Thistle, Bittermelon, White Kidney Bean extract;

Vitamins/Minerals: Vitamin C, B-vitamins (various), Vitamin A, Calcium, Selenium;

Various nutrients: Alpha-Lipoic-Acid, Anthocyanins (can vary), Curcumin, Butyrate, Glutamine.

C. Predicted Glycemic Response

The dataset analyzed by the recommendation engine can include an entry for predicted glycemic response of a subject to. One such method is described in U.S. provisional patent application 62/804,737, filed Feb. 12, 2019. In one such method, data are collected from a plurality of study participants, each of whom has consumed one or more foods/meals over the course of the study. Raw data used to build a training dataset can include various kinds of -omic data such as gut microbiome genomic or transcriptomic data, blood transcriptomic data and/or urine metabolism of data. Such data can be abstracted into features that describe types and amounts of microbes in a subject's microbiome as well as gene expression levels and/or activity of biochemical pathways. Also included in the dataset are phenotype data about each individual subject. Such data can be abstracted from responses by subjects to questionnaires. Meal data for each subject can include data about each meal consumed by a subject during the study. Meal data can include macronutrient and micronutrient information about each meal/food as well as the time of consumption. The dataset can also include activity/sleep data indicating amount and/or quality of sleep, timing of sleep, amount and/or intensity of physical activity and its timing. Glycemic response data can include raw glycemic response data that provides a quantitative measure of blood glucose levels in response to consumption of a meal. Such data can be abstracted to classify the glycemic response. Classifications can be discreet (e.g., high or low, or on a numeric scale) or continuous (e.g., on a continuous scale). In some cases, the dimensionality of the data can be reduced to make it more tractable for a learning algorithm. A machine learning algorithm can be trained on the dataset to generate one or more models that predict the glycemic response of an individual to a food based on the food's macronutrient profile, the subject's phenotypic data and omic data from the subject. A macronutrient profile can include absolute or relative amounts of each of a plurality of macronutrients in a food or meal, on, for example, a mass or calorie basis.

In the dataset, predicted glycemic response can be assigned a positive or negative desirability rating, e.g., "enjoy" or "minimize". This rating can be used as another food ratings, e.g., a rating of "minimize" is prioritized over "enjoy" or "superfood".

D. Food Sensitivity Information

In certain embodiments, information regarding sensitivity to a particular food antigen or antigens may also be used in the systems and methods presented herein. Without being bound by theory, it is thought that, for a given individual, certain foods or food antigens may cause sensitivity in the individual to that food or food antigen, e.g., mediated by IgG binding. Thus, in certain embodiments, information for an individual may include information regarding food sensitivities of the individual. This may involve testing at least 1, 2, 5, 10, 15, 20, 30, 40, 50, 70, 100 or more than 100 food antigens for reaction with a sample from the individual, such as blood, urine, hair, skin, or any suitable sample, e.g., a blood sample or sample derived from a blood sample such as serum or plasma. Any suitable method of determining sensitivity may be used, for example, an ELISA test or microbead-based assay, where a surface is coated with a ground-up food (food antigen) and IgGs from serum/plasma are allowed to bind to the antigens, and the presence of bound IgGs is detected.

In the dataset, food sensitivities can be assigned a negative desirability rating, e.g., "high sensitivity". A rating of high sensitivity can take priority over other desirability ratings, producing a final recommendation of "avoid".

V. Personalized Food Recommendations

To determine a predicted effect of a food on an individual, which corresponds to its desirability, and, in turn, the recommendation for that food, its predicted effect on some or all of the biological conditions of the individual may be assessed. It will be appreciated that the same food may be beneficial for some biological conditions and detrimental for others, all of which may be present in the same individual. The predicted effects of the food on the biological conditions of interest may be combined to give an overall predicted effect, or desirability, and in turn a recommendation, for the food for the individual. The process of combining the predicted effects/desirability/recommendation may be any suitable process. In certain embodiments, the most negative effect, e.g., the effect that leads to the least desirability and lowest recommendation among the effects/desirability/recommendations predicted for the biological conditions considered, is chosen. However, other processes may be used for combining different effects/desirability/recommendations for the same food for different biological conditions in an individual. For example, the effects/desirability/recommendations for some conditions may be weighted more heavily than others. As an example, in the case of a food that is highly effective at improving cardiovascular condition, and thus would have a "superfood" designation for cardiovascular condition, but that also causes an increase in acne, and thus would have a "minimize" or "avoid" designation for acne, the effect on cardiovascular condition could be weighted, e.g., 10-fold more heavily than the effect on acne, and the combined designation would still be "superfood." This is merely exemplary and any suitable method of weighting effects/desirability/recommendations for different biological conditions may be used, or any other suitable method for combining effects/desirability/recommendations when they are different for different biological conditions in an individual.

Typically, a recommendation engine will execute logic by computer to combine desirability ratings of a food, supplement or ingredient to make a final desirability recommendation. Exemplary rules for such a logic are described herein.

In addition, the database can indicate, for each food or supplement in the database, a predicted glycemic response to the food or supplement.

In addition, the database can indicate, for each food or supplement, whether the subject has an adverse sensitivity to the food or supplement.

An automated program may be used to keep track of assessments for a given food and, when a final rating for that food is reached, place the rating on a list of foods that includes the given food, and, optionally, translate the bases of the rating to text that gives an explanation to the user of the food lis as to why the given food was assessed with its rating. Generally, the text will be at a level that can be understood by a layman without expertise in the technical knowledge used in the algorithm. Thus, at the end of the process, a list of foods may be generated where the list includes foods, a recommendation for at least some of the foods, e.g., for each food on the list (e.g., "superfood," "enjoy," "minimize," or "avoid," or any other suitable system of recommendation), and, optionally, for some or all of the foods, an explanation in language understandable to the layman as to why each food was given its particular recommendation. The list of foods may include at least 2, 5, 10, 25, 50, 75, 100, 150, 200, 250, or 300 different foods; in some cases, some or all of the foods are given a rating (e.g., "superfood (indulge)," "enjoy," "minimize," or "avoid," or any other suitable system of recommendation), and in some cases, some or all of the ratings include an explanation in language understandable to the laymen as to the reasons for the rating. The explanation may include information as to one or more biological conditions of the individual, and/or one or more effects of one or more biological conditions, and how and why the food was rated as related the biological condition and/or effects of the condition. In some cases, all ratings may be explained. In some cases, only some ratings may be explained, for example, foods with the designation "superfood (indulge)" or "avoid" may be explained. The list may be provided in any suitable form, such as one or more of a paper listing, a listing on a website where a user can find their individual listing, a listing on an application ("app"), and the like.

To determine the effects/desirability/recommendations for a food for a biological condition, any suitable method may be used. For example, a combination of one or more of the effects/desirability/recommendations of macronutrients in the food on the condition, the effects/desirability/recommendations of specific compounds in the food on the condition, and the effects/desirability/recommendations of interaction of the food with the microbiome may be assessed.

A food may be assigned to a food group and the effects of the group may be assessed. For example, milk can belong to the non-fermented dairy food group, and yogurt belongs to the fermented dairy group or fermented food group. A food may belong to no food group, only one food group, or more than one food group; in certain embodiments, a food belongs to only no food group or one food group; i.e., food groups are non-intersecting subsets of the entire set of foods examined. In certain embodiments, one or more food groups may be based on the relevance of the foods in the group to certain conditions. For example, a fermentable sugars food group (foods containing significant levels of fermentable sugars) is relevant to the biological condition of small intestinal bacterial overgrowth (SIBO).

In certain embodiments, the effects/desirability/recommendations of macronutrients in the food (or food group to which the food belongs) for a given biological condition are assessed. In some cases, macronutrient effects/desirability/recommendations are assessed first. Macronutrients used in this analysis can include any suitable group of macronutrients, such as carbohydrates, fiber (generally indigestible carbohydrates), proteins, and fats. The food (or food group) is given a first recommendation based on the likely effect of its macronutrients on the biological condition. The recommendation may be one of two, three, four, or more than four possible recommendations, for example, the recommendation may be one of three possible recommendations, such as "enjoy," "minimize," or "avoid." For example, if an individual is found to have the biological condition of dysglycemia (hyperglycemia), the food beet sugar, whose macronutrient content is entirely simple carbohydrates, would receive a rating at this step of "avoid." Thus, in certain cases, the effects of macronutrients in the food or food group on the biological condition may be so detrimental that the food or food group receives a recommendation of "avoid" based solely on macronutrient content, and no further assessment may be performed. If the rating is "minimize" or "enjoy," further steps may be performed to determine a final rating.

The effects/desirability/recommendations of specific compounds in the food on the biological condition can alternatively or additionally be assessed. In certain embodiments, this assessment comes after the assessment for macronutrient effects/desirability/recommendations. Specific compounds in the food can include micronutrients, as well as other relevant compounds that are not micronutrients, such as purines. Exemplary specific compounds whose effects can be assessed in this step are shown in Table 4. Micronutrients can include, for example, a mineral, a trace mineral, a vitamin, a biochemical substrate, or any combination thereof. A mineral may be calcium, magnesium, sulfur, or any combination thereof. A trace mineral may be iron, chromium, copper, fluoride, iodine, manganese, molybdenum, selenium, zinc, or any combination thereof. A vitamin may be thiamin (B1), riboflavin (B2), niacin, Vitamin B6, cobalamin (B12), folate, ascorbic acid, Vitamin A, Vitamin D, Vitamin E, Vitamin K, or any combination thereof. It will be appreciated that a given food or food group may have a large variety of specific compounds and one or more of the specific compounds may affect a biological condition; a database of foods, food groups, and conditions may be established that indicates the effects/desirability/recommendations of the typical specific compound profile of the food or food group on a particular condition. In certain cases, foods are classified based on the presence of 1, 2, 3, 4, 5, or more than 5 specific compounds, for example, one specific compound. In the latter case, for example, a food may be classed as a purine-containing food based on its typical purine content, regardless of its content of other specific compounds. The predicted effects/desirability/recommendations of the food or food group on the biological condition is assessed based on its specific compound profile, and the recommendation based on macronutrients may remain the same, or it may be upgraded or downgraded. For example, a food or food group can move from "enjoy" to "superfood," or from "minimize" to "avoid," or from "minimize to enjoy," etc. In certain cases, the rating for a food or food group can change up to 2 levels (e.g., from "enjoy" to "avoid"), or one level (e.g., a food can change from "minimize" to "enjoy" but not from "minimize" to "superfood"), or a combination thereof. In some cases, a food may be downgraded but not upgraded, or only upgraded to the level of "enjoy."

TABLE 4

Exemplary Specific Compounds

| | | |
|---|---|---|
| Adenine Nutrient | Aglycone | Absorbable Carbohydrate Allergen Protein |
| Allicin | Alliin | Allyl Cysteine |
| Alpha Linolenic Acid | amino acids | Anethole |
| Anthocyanidin Nutrient | Anthocyanin | Apigenin |
| Arginine | Ascorbic Acid | Avenanthramide |
| Avenanthramide Nutrient | Avenanthramide PhenolicAcid | B carotene |
| B vitamins | Beta Carotene | Beta Glucan Cereal |
| Biotin | Butyrate | Butyric Acid |
| Caffeine | Caffeine Nutrient | Calcium |
| Calcium Ion2 | Capsaicin | Casein1 |
| Casein2 | Catechin | Cholesterol |
| Choline | Citrulline | Cobalamin |
| CoEnzymeQ10 | Collagen | |
| | | Cyanidin |
| Cysteine | Daidzein | Delta-7-sterine |
| Deta-sitosterol | DodecanoicAcid (LauricAcid) | EGCG |
| EicosaPentanoicOmega3 | ELLAGIC | EllagicAcid |
| Epicatechin | Epigallocatechin Gallate | Essential fatty acids |
| Fatty Acid | Fatty Acid | ferulic acid |

TABLE 4-continued

Exemplary Specific Compounds

| | | |
|---|---|---|
| Nutrient_Omega3 | Nutrient_Omega9 | |
| fiber | FlavonoidNutrient | folate |
| folic acid | FOS | FructOligoSaccharide |
| Fructose | GalactOligoSaccharide | GamaAminoButyricAcid |
| GammaAminoButyricAcid | GammaLinolenicAcid | gingerol |
| GingerolNutrient | GLA | Glucobrassicin |
| Glucoraphanin | GlucosinolateNutrient | glucosinolates |
| Glutamine | GLUTEN | GlycemicIndex |
| | GlycemicIndex/Glycemic Load | glycoside |
| GuanineNutrient | HypoxanthineNutrient | Inulin |
| iodine | IodineNutrient | iridoid glycoside |
| iron | IronIon2 | kampferol |
| Lactalbumin Alpha | Lactalbumin Beta | Lactose |
| lauric acid | Lectin | Lignan Nutrient |
| Limonin Glucoside | Linalool | Linoleic Acid |
| Lutein | Lutein Zeaxanthin | Luteolin |
| Lycopene | magnesium | Magnesium Ion2 |
| Maltose | Mannitol | medium chain triglycerides |
| Medium Chain Fatty Acid Nutrient | Mucilage | MUCIN |
| MUFAs | Naringenin | niacin |
| Nitrate | Nitrite | OleicAcid |
| OXALATE | pantothenic acid | phospholipids |
| phosphorus | Phytonutrient Nutrient | phytonutrients |
| Phytosterol Nutrient | phytosterols | Polyphenol Nutrient |
| polyphenols | PolysaccharideInsoluble Fiber Nutrient | Polysaccharide Insoluble Nutrient |
| Polysaccharide Soluble Fiber Nutrient | Polysaccharide Soluble Nutrient | potassium |
| Potassium Ion | Potassium Ion1 | probiotics |
| protein | pyridoxine | Quercetin |
| Resistant Starch Nutrient | resveratrol | Retinoid Nutrient |
| riboflavin | S Adenosyl Methionine | Saponin Glycoside |
| Saponin Phytonutrient | saponins | Saturated Triacylglycerol Fat |
| selenium | Selenium Nutrient | Sesquiterpene Lactone |
| Sinigrin | sodium | SodiumIon1 |
| Sorbitol | Tannoid Nutrient | Theanine |
| Theobromine Nutrient | Theophylline Nutrient | thiamin |
| thiamine | thiols | Total Anthocyanidin |
| Total Carbohydrate By DifferenceNutrient | Total Copper | Total Fiber Carbohydrate Nutrient |
| Total FructoOligosaccharide | Total GalactoOligosaccharide | Total Goitrogen |
| Total Inulin | Total Iron | Total Oxalate |
| Total Phosphorous | Total Polyphenol | Total Protein |
| Total Purine | Total Sulfur | Tryptophan |
| VitAIU | Vitamin C | Vitamin E |
| Vitamin A | Vitamin B12 | Vitamin B6 |
| Vitamin C | Vitamin D | Vitamin E |
| Vitamin K | VIT B | VITB2_Total Riboflavin |
| VITB3_Total Niacin | VITB5_Total PantothenicAcid | VITB6_Total PLP |
| VITB9 | VITB9_Total Folate | VITE |
| VITK_TotalMK | XanthineNutrient | Zeaxanthin |
| Zinc | Zinc Ion2 | |

The effects/desirability/recommendations of the food in relation to the microbiome can alternatively or additionally be assessed. In certain embodiments, combined effects of foods or food groups and microbiome on biological conditions are assessed. In other embodiments, foods are assessed without reference to biological conditions; e.g., a food or food group that has already been assigned a rating for an individual, such as by assessment of macronutrients and/or specific compounds, is assessed to see if microbiome effects will alter the rating. In some cases, the rating can remain the same, be upgraded, or be downgraded, depending on the individual's microbiome. In some cases, the rating can remain the same or be downgraded depending on the individual's microbiome. Any suitable method of determining a microbiome effect for a given individual may be used. In certain cases, microorganisms (used herein to include viruses) are assessed at any suitable level, such as at the genus, species, or strain level. In certain cases, microorganisms assessed include one or more of bacteria, fungi, archaebacteria, viruses, protists, or any combination thereof. In certain cases, bacteria and viruses are assessed. In certain cases, bacteria, viruses, and fungi are assessed. In certain cases, bacteria, viruses, and archaebacteria are assessed. In certain cases, bacteria, fungi, viruses, and archaebacteria are assessed. One or more microorganisms may be assessed, e.g., at least 1, 2, 3, 4, 5, 6, 7, or 8 microorganisms. The microorganism or microorganisms may be assessed at the genus, species, or strain level, or any combination thereof. The assessment can be any suitable assessment. For example, the assessment may be based partially or entirely on the presence or absence of one or more microorganisms, for example, at the genus or species level. The assessment can be further refined in terms of quantity or relative quantity of the microorganism or microorganisms, and if more than one microorganism is assessed, the different microorganisms may be weighted or otherwise manipulated in producing a final recommendation. In certain embodiments, the assessment of the microbiome is used at least in part to determine whether a particular food or food group or components thereof will be altered by the microorganism or microorganisms, in such a way as to be beneficial or detrimental. For example, if the food spinach is rated as "enjoy" after an initial assessment, such as assessment of macronutrients and specific compounds, the presence or absence of the genus Oxalobacter and/or species Oxalobacter formigenes, which acts on the oxalate in spinach, may be assessed. If the genus/species is present, then spinach remains at "enjoy," but if absent, spinach is downgraded to "minimize." Thus, in this case, the absence (or low levels) of a microorganism causes the food rating to be downgraded. Another example is if the microbiome contains pepper mild mottle virus, the recommendation for bell peppers may be downgraded. In this case, the presence (or high levels) of a microorganism may cause the food rating to be downgraded.

The effects of a food or food group on food sensitivities in the individual may additionally or alternatively be assessed, and used to determine and/or modify food recommendations for the individual as appropriate. In certain cases, one or more food sensitivities for the individual may be used to modify food recommendations. In certain cases, although food recommendations are not modified based on one or more food sensitivities, the individual is informed of the one or more food sensitivities; for example, the individual may be informed of their level of sensitivity to a food, which can be one of at least 1, 2, 3, 4, or more than 4 levels; e.g., levels of sensitivity can be designated as "none," "low," "medium," or "high," and the individual informed of the designation; additionally, the individual may be informed that a food contains antigens from relevant foods (e.g., kefir contains yeast, milk, whey, and casein). A combination of the two approaches may be used. In certain embodiments, after a food or food group has been given a designation based on, e.g., macronutrient, specific compounds, and/or microbiome, food sensitivity information is used to modify recommendations as needed; in certain cases, food sensitivity for a particular food may be ranked in terms of severity and that information can inform whether or not, and/or to what degree, to modify food recommendations. Food sensitivity test results can be used to move a food from a higher consumption recommendation to a lower one, due to a positive test for the specific food; for example, a food can be moved from the "enjoy" to "minimize" or "avoid" category if it is found that the individual is sensitive to that food; the decision to alter the recommendation, and/or the degree to which the recommendation is altered, may be determined by any suitable method, e.g., if an individual is found to be highly sensitive to a particular food it may be moved more than one rank in recommendation, such as from "enjoy" to "avoid;" alternatively or in addition, a higher sensitivity to a particular food may cause a larger set of foods to be downgraded in recommendation than a lower sensitivity to the food. In certain cases, foods known to cross-react with a particular food to which the individual is found to be sensitive may also have their recommendation altered (and/or the individual alerted to the cross-reactivity). For example, if a person is found to be sensitive to tuna, the recommendation for cross-reactive food such as salmon may be adjusted, e.g., moved downward, based on the cross-reactivity. In certain cases, multiple foods can belong to a food group whose recommendations may be altered by the sensitivities of an individual to foods within the group. For example, if an individual tests as sensitive to tomato, pepper, and potato, which are members of the nightshade family, this could affect additional nightshade-related recommendations; whether or not, and/or to what degree, recommendations for foods in a food group are altered based on food sensitivities to members of the group may depend on how many foods in the group the individual is sensitive to and/or the severity of the sensitivity. In certain cases, recommendations for foods to which the individual is not sensitive may be affected by the food sensitivity information. A food to which the individual is not sensitive can be moved to a higher level of recommendation because it possesses one or more characteristics that overlap with those of a food to which the individual is sensitive. This can be based on macronutrient and/or specific compound (e.g., micronutrient) composition of the respective foods. For example, if two foods both contain a necessary micronutrient, they may initially be placed in the "enjoy" category; if an individual is found to be sensitive to one but not the other, the food to which the individual is sensitive may be downgraded to "minimize" or "avoid," while the food to which the individual is not sensitive may be upgraded to "indulge" (e.g., superfood).

In certain embodiments, only one of predicted effects/desirability/recommendations of macronutrient, specific compound, or microbiome of a particular food or food group is used to generate a recommendation for a food. In certain embodiments, two of predicted effects/desirability/recommendations of macronutrient, specific compound, or microbiome of a particular food or food group is used to generate a recommendation for the food. In certain embodiments, all three of predicted effects/desirability/recommendations of macronutrient, specific content, or microbiome of a particular food or food group is used to generate a recommendation for the food.

As discussed above, when more than one biological condition is present, a given food or food group may generate more than one recommendation, and the recommendations may be combined in any suitable manner, such as choosing the most restrictive recommendation. Thus, one or more of assessment for a food of macronutrient, specific compound, and/or microbiome effects may be performed for any suitable number of biological conditions in an individual, such as 1, 2, 3, 4, 5, or more than 5 conditions, depending on the number of conditions for the individual, and the recommendations for the food for the different conditions can be combined as described herein.

Supplements may be classified as probiotics, digestive support, polyphenols, gut support, digestive enzymes, antioxidants, prokinetic, or prebiotic. See Table 3 for an exemplary list of supplements. For supplement recommendations, microbiome features are considered, and the presence or absence of certain microbes, and in some cases relative abundances or other microbiome information, is used to determine supplement recommendations.

In classifying a food based on its desirability for a subject, the recommendations for the food for each biological condition for which the subject is sub-optimal can be taken into account. Various algorithms can be used for this purpose. For example, a value of central tendency (e.g., average or variance) of all the recommendations for all sub-optimal biological conditions can be used. For example, if the values for four biological conditions, or a scale of 1-4 are 3, 2, 4 and 4, the designation could be the average, in this case, 3.25, which might be rounded to "3". Scores can be weighted, that scores for certain conditions count for more than other conditions. For example, a score for inflammatory activity might be given twice the weight of a score for gas production.

In one embodiment, the final score is assigned based on a logic that uses a hierarchical process of elimination. In one such method, it is determined whether the food has a least beneficial rank designation for any biological condition present; if so, that rank is assigned as the food recommendation for the subject. If no biological conditions are so ranked, it is determined whether the food has a next higher rank designation for any biological condition present; if so, that next higher rank is assigned as the food designation. This process continues for increasingly beneficial rankings.

In a related embodiment, foods are assigned one of four rankings for each condition present. These maybe called, from lowest desirability to highest desirability, for example, "avoid", "mimimize", "enjoy" and "superfood". In addition, the food is assigned to a glycemic response category for the subject, which may qualify as "high" or "low" (or "high", "medium" or "low"). In a first pass, it is determined whether the food is categorized at the least beneficial level ("avoid") for any condition. If so, the food is designated "avoid" for the subject. If the food is not designated "avoid" for any condition, then, in a second pass, it is determined whether the food is categorized as "minimize" (including a "high" predicted glycemic response) for any condition. If so, the food is categorized as "minimize" for the subject. If the food is not designated "minimize" for any condition, then, in a third pass, it is determined whether the food is categorized as "superfood" for any condition. If so, the food is categorized as "superfood" for the subject. If the food is not categorized as "avoid", "minimize" or "superfood" for any condition present, then the food is designated as "enjoy" for the subject.

FIG. 4 shows an exemplary application of recommendation engine uses logic as described herein to provide final recommendations for a variety of food items. Knowledge database includes for each of a plurality of phenotypic conditions and functional activity conditions, a desirability rating for each of a plurality of foods, supplements and ingredients. Omic data has been used to infer the presence of biological conditions in a subject. In this case, phenotype condition to, functional activity conditions one, and functional activity condition n are present. Non-present biological conditions, i.e., phenotype condition 1, phenotype conditions 3, phenotype condition and, functional activity condition 2, and functionally activity condition 3 are not present in our greyed-out.

Food 1 has a desirability rating of "avoid" for functional activity condition 1. This rating takes priority over all of the ratings. Therefore, food 1 is given a final recommendation of "avoid".

Food 2 has no desirability ratings of "avoid" but does have a desirability rating of "minimize" for functional activity condition n. Therefore, it is assigned a final recommendation rating of "minimize".

Food 3 has no desirability ratings of "avoid" or "minimize", but does have a desirability rating of "superfood" for functional condition 1. Therefore, it is assigned a final recommendation rating of "superfood".

Food 4 has no desirability ratings of "avoid" "minimize" or "superfood". Therefore, it is assigned a final recommendation rating of "enjoy".

Food 5 has a desirability rating of "minimize" for the subject's predicted glycemic response to the food. Therefore, it is assigned a final recommendation of "minimize".

Supplement 1 has a desirability rating of "not recommended" for functional activity condition n. Therefore, it is assigned a final recommendation of "not recommended".

Supplement q has a desirability rating of "recommended" for functional activity condition 1, but no ratings of "not recommended". Therefore, it is assigned a final recommendation of "recommended".

Ingredient 1 has a desirability rating of "avoid" for functional activity condition 1. Because the negative desirability rating priority over other desirability ratings, this ingredient is assigned final recommendation of "avoid".

Ingredient r has a desirability rating of "super ingredient" for phenotype condition 2, but no negative desirability ratings. Therefore, this ingredient is assigned final recommendation of "super ingredient".

Recommendations for altering diet can be provided to a subject in electronic or paper format. Electronic communications can be communicated to the subject over a communications network to an electronic device accessible by the subject. Data can be transmitted electronically, e.g., over the Internet. Communication may be, for example, in the form of information provided on a password-protected website accessible by the subject. Alternatively, communication may be by email or text message. Electronic devices accessible by the subject can include, for example, computers connected to the Internet, smart phones (e.g., iPhone® or Samsung Galaxy®), or a wearable device (e.g., Fitbit® or Garmin®). Electronic communication can be, for example, over any communications network include, for example, a high-speed transmission network including, without limitation, Digital Subscriber Line (DSL), Cable Modem, Fiber, Wireless, Satellite and, Broadband over Powerlines (BPL). Information can be transmitted to a modem for transmission e.g. wireless or wired transmission, to a computer such as a desktop computer. Alternatively, reports can be transmitted to a mobile device. Reports may be accessible through a subscription program in which a user accesses a website which displays the report. Reports can be transmitted to an electronic device accessible by the user. This could be, for example, a personal computer, a laptop, a smart phone or a wearable device, e.g. worn on the wrist.

The diet of a subject refers to the total kind and quantities of food, supplements, probiotics, and medicines consumed by a subject over a defined period of time e.g., over the course of about a day, about a week, about a month or about a year. A diet can be further defined in terms of macronutrient and micronutrient content. Macronutrients include, for example, carbohydrates, fiber (generally indigestible carbohydrates), proteins, and fats. Macronutrients used in this analysis can include any suitable group of macronutrients, such as carbohydrates, fiber (generally indigestible carbohydrates), proteins, and fats. Micronutrients include, for example, a mineral, a trace mineral, a vitamin, a biochemical substrate, or any combination thereof. A mineral may be calcium, magnesium, sulfur, or any combination thereof. A trace mineral may be iron, chromium, copper, fluoride, iodine, manganese, molybdenum, selenium, zinc, or any combination thereof. A vitamin may be thiamin (B1), riboflavin (B2), niacin, Vitamin B6, cobalamin (B12), folate, ascorbic acid, Vitamin A, Vitamin D, Vitamin E, Vitamin K, or any combination thereof.

Altering the diet of the subject can alter activity in any number of functional categories, resulting in desired changes in either specific microbial pathways and/or broader biological functions of the microbiome or of the host (based on the microbiome). In general, an aim of altering diet is to rebalance the microbiome of a subject such that functional activity scores shift toward or into the reference range. This can be accomplished by several means. One method is to provide dietary items that promote the production of useful nutrients by the gut microbes. Another method is to reduce or avoid foods high in nutrients that are used by the microbes to produce harmful products. Another method is to provide a food or supplement containing probiotic microbes that produce beneficial nutrients or "overpower" the harmful microbes or the activity levels of microbial pathways that yield harmful products. Another method is to provide the beneficial macro- and/or micronutrients directly in the available forms of diet and supplement recommendations.

VI. Food and Supplement Delivery

In another aspect, after determining that a functional activity score of a subject is outside reference range, one or more of a food, a supplement, a probiotic or a medicine can be identified which, when included in the diet of the subject, shifts the functional activity score toward or into the reference range. So, for example, if it is determined that a subject has an inflammatory activity score that is high compared with the reference range, dietary items that will decrease the inflammatory activity score can be identified. These might include, for example, foods or supplements high in antioxidants or probiotics including microbes that depress pro-inflammatory biochemical pathways, such as the butyrate pathway.

These dietary items can be delivered to a subject, for example, via common carrier. Such items can be provided in a kit, which typically includes a collection of items intended for use together. Kits can include containers to hold dietary items. Containers, themselves, can be placed into a shipping container, such as a box or a bag. The container can be transmitted by hand delivery or by a common carrier, such as a national postal system or a delivery service such as UPS or FedEx. Kits can also typically include written recommendations or instructions for use.

VII. Exemplary Embodiments

1. A method of determining recommendations of desirability of a plurality of different foods for an individual, wherein the individual has an individual set of biological conditions comprising at least 1 biological condition, and wherein the recommendation for each food is based on its predicted effect on the at least 1 biological condition. 2. The method of embodiment 1 wherein the individual set of biological conditions comprises at least 2 biological conditions, and wherein the recommendation for each food is based on combining recommendations for the food for each of the two conditions. 3. The method of embodiment 1 wherein the individual set of biological conditions comprises at least 3 biological conditions, and wherein the recommendation for each food is based on combining recommendations for the food for each of the 3 conditions. 4. The method of embodiment 1 wherein the individual set of biological conditions comprises at least 4 biological conditions, and wherein the recommendation for each food is based on combining recommendations for the food for each of the 4 conditions. 5. The method of embodiment 1 wherein the individual set of biological conditions comprises at least 5 biological conditions, and wherein the recommendation for each food is based on combining recommendations for the food for each of the 5 conditions. 6. The method of embodiment 1 wherein the condition is determined from an overall set of biological conditions. 7. The method of embodiment 1 wherein the plurality of different foods comprises at least 2, 5, 10, 20, 30, 40, 50, 70, 100, 120, 150, 170, 200, 250, or 300 different foods. 8. The method of embodiment 1 wherein the recommendation of desirability of the plurality of different food comprises at least 2, 3, or 4 discrete values of desirability, wherein the values are in order of decreasing desirability. 9. The method of embodiment 1 wherein, if a recommendation of desirability of a food for any of the at least 2 biological conditions is different from the others, a final recommendation is determined by choosing the most restrictive recommendation. 10. The method of embodiment 1 wherein the individual set of biological conditions comprises at least 2, 3, 4, 5, 6, 7, 8, 9 or 10 biological conditions, and wherein the recommendation for each food is based on its predicted effect on at least some of the biological conditions in the individual set of biological conditions. 11. The method of embodiment 10 wherein the recommendation for each food is based on its predicted effect on at least ¼, ½, or ¾ of the biological conditions in the individual set of biological conditions. 12. The method of embodiment 1 wherein the individual is determined to have an individual set of biological conditions based on phenotype and microbiome information for the individual. 13. The method of embodiment 12 wherein the phenotype information is obtained in a process comprising determining response for the individual to a questionnaire. 14. The method of embodiment 12 wherein the microbiome information is obtained from a sample from the individual. 15. The method of embodiment 14 wherein the sample is a stool sample. 16. The method of embodiment 12 wherein the microbiome information comprises transcriptome information. 17. The method of embodiment 12 wherein the microbiome information comprises information regarding viruses in the microbiome. 18. The method of embodiment 1 wherein determining a recommendation for desirability of consumption of a first food of the plurality of foods for the individual comprises performing at least one of (i) predicting an effect of macronutrient content of the first food on a first biological condition in the individual and determining a first recommendation based on the predicted effect of macronutrient content of the food; (ii) predicting an effect of one or more specific compounds in the first food on the first biological condition in the individual and determining a second recommendation based on the predicted effect of the one or more specific compounds; and (iii) predicting an effect of the first food on a microbiome of the individual, and determining a third recommendation based on the predicted effect on the microbiome. 19. The method of embodiment 18 comprising performing at least two of steps (i)-(iii). 20. The method of embodiment 18 comprising performing all of steps (i)-(iii). 21. The method of embodiment 20 wherein steps (i), (ii), and (iii) are performed in sequential order. 22. The method of embodiment 21 wherein a food is given a first recommendation after step (i), then step (ii) is performed and the food is given a second recommendation, wherein the second recommendation can be the same as the first recommendation or an upgrade or downgrade of the first recommendation, then step (iii) is performed and the food is given a third recommendation, wherein the third recommendation can be the same as the second recommendation or an upgrade or downgrade of the second recommendation. 23. The method of embodiment 1 wherein desirability for consumption of a food can have at least 2, 3, or 4 values. 24. The method of embodiment 23 where the values are graded in terms of desirability. 25. The method of embodiments 18, 19, or 20, further comprising performing one or more of steps (i)-(iii) for a second biological condition, where the second biological condition is different from the first, and determining a recommendation for desirability of consumption of the food for the second biological condition. 26. The method of embodiment 25 wherein at least one of steps (i)-(iii) is performed for the second biological condition. 27. The method of embodiment 25 wherein at least two of steps (i)-(iii) is performed for the second biological condition. 28. The method of embodiment 25 wherein at all three of steps (i)-(iii) is performed for the second biological condition. 29. The method of embodiment 28 wherein steps (i)-(iii) are performed sequentially. 30. The method of embodiment 25 further comprising combining the recommendations for desirability of consumption of the food for the first biological condition and for the second biological condition to determine a combined desirability for consumption of the food. 31. The method of embodiment 25 wherein the combining comprises determining whether one recommendation for desirability is more restrictive than the other, and, if so, determining that the combined desirability for consumption of the food is the more restrictive desirability. 32. The method of embodiment 25 further comprising performing one or more of steps (i)-(iii) for a third biological condition, where the third biological condition is different from the first and second biological conditions, and determining a recommendation for desirability of consumption of the food for the third biological condition. 33. The method of embodiment 32 wherein at least one of steps (i)-(iii) is performed for the third biological condition. 34. The method of embodiment 32 wherein at least two of steps (i)-(iii) is performed for the third biological condition. 35. The method of embodiment 32 wherein at all three of steps (i)-(iii) is performed for the third biological condition 36. The method of embodiment 35 wherein steps (i)-(iii) are performed sequentially. 37. The method of embodiment 32 further comprising combining the recommendations for desirability of consumption of the food for the first, second, and third biological conditions to determine a combined desirability for consumption of the food. 38. The method of embodiment 37 comprising determining which if any, of the recommendations for desirability of consumption of the food is most restrictive, and, if so, determining that the combined desirability for consumption of the food is the most restrictive desirability. 39. The method of embodiment 32 further comprising performing steps (i)-(iii) for a fourth biological condition, where the fourth biological condition is different from the first, second, and third biological conditions, and determining a recommendation for desirability of consumption of the food for the fourth biological condition. 40. The method of embodiment 39 wherein at least one of steps (i)-(iii) is performed for the fourth biological condition. 41. The method of embodiment 39 wherein at least two of steps (i)-(iii) is performed for the fourth biological condition. 42. The method of embodiment 39 wherein all three of steps (i)-(iii) is performed for the fourth biological condition. 43. The method of embodiment 42 wherein steps (i)-(iii) are performed sequentially. 44. The method of embodiment 39 further comprising combining the recommendations for desirability of consumption of the food for the first, second, third, and fourth biological conditions to determine a combined desirability for consumption of the food. 45. The method of embodiment 44 comprising determining which if any, of the recommendations for desirability of consumption of the food is most restrictive, and, if so, determining that the combined desirability for consumption of the food is the most restrictive desirability. 46. The method of any of embodiments 18 through 45 further comprising determining a recommendation for desirability of consumption of a second food from the plurality of foods, wherein the second food is different from the first, comprising performing one or more of steps (i)-(iii) for the second food, for at least 1, 2, 3, 4, or 5 biological conditions from the individual set of biological conditions. 47. The method of any of embodiments 18 through 45 wherein one or more of steps (i)-(iii) are performed for at least 2, 5, 10, 20, 50, 100, 150, 200, 250, or 300 different foods. 48. The method of any of embodiments 1 through 47 wherein one or more of the foods are classed as part of a food group and the prediction of one or more of steps (i), (ii) and/or (iii) is based on the food group. 49. The method of any of the previous embodiments further comprising providing an explanation for the recommendations for at least some of the foods to the individual, wherein the recommendation is determined from results of one or more steps of analysis of the food and its effect on one or more conditions of the individual. 50. The method of embodiment 50 wherein the explanation is provided as text suitable to layman understanding.

51. A method of determining a set of food recommendations for an individual comprising (i) determining an individual set of one or more biological conditions for the individual from an overall set of biological conditions by combining phenotype and microbiome information for the individual; and (ii) determining the food recommendations for the individual based on the predicted effects of foods and/or food groups on one or more of the conditions for the individual. 52. The method of embodiment 51 wherein the microbiome information includes transcriptome information. 53. The method of embodiment 51 or 52 wherein the microbiome information includes taxa information and gene expression information. 54. The method of embodiment 52 wherein the microbiome information includes one, two, three, four, or all of information regarding bacteria, viruses, archaebacteria, fungi or protists. 55. The method of embodiment 51 wherein the predicted effects comprise macronutrient effects, specific compound effects, microbiome effects, or any combination thereof 56. The method of embodiment 51 wherein, if predicted effects of a food or food group lead to different recommendations for a food for different conditions, the most restrictive recommendation is chosen as the final recommendation.

57. A method of determining a recommendation for desirability of consumption of a first food for an individual comprising performing at least one of (i) predicting an effect of macronutrient content of the first food on a first biological condition in the individual and determining a first recommendation based on the predicted effect of macronutrient content of the food; (ii) predicting an effect of specific compound content of the first food on the first biological condition in the individual and determining a second recommendation based on the predicted effect, wherein the second recommendation can be the same as or different from the first recommendation, depending on the micronutrient effect; and (iii) predicting an effect of the first food on a microbiome of the individual, and determining a third recommendation based on the predicted effect, wherein the third recommendation can be the same as or different from the second recommendation, depending on the microbiome effect. 58. The method of embodiment 57 wherein microbiome information includes information regarding the presence or absence, quantity, or other characteristic of one, two, three, four, or all of bacteria, viruses, archaebacteria, fungi, or protists that may be affected by the first food. 59. The method of embodiment 57 comprising performing at least two of steps (i)-(iii). 60. The method of embodiment 57 comprising performing all of steps (i)-(iii). 61. The method of embodiment 57 wherein steps (i), (ii), and (iii) are performed in sequential order. 62. The method of embodiment 57 wherein desirability for consumption of a food can have at least 2, 3, or 4 values. 63. The method of embodiment 62 where the values are graded in terms of desirability. 64. The method of embodiment 57 further comprising performing one, two, or all of steps (i)-(iii) for a second biological condition, where the second biological condition is different from the first, and determining a recommendation for desirability of consumption of the food for the second biological condition. 65. The method of embodiment 64 further comprising comparing the recommendation for desirability of consumption of the food for the first biological condition and for the second biological condition to determine which, if either, is more restrictive, and determining a final recommendation for desirability of the food that is the more restrictive desirability. 66. The method of embodiment 64 further comprising performing one, two, or all of steps (i)-(iii) for a third biological condition, where the third biological condition is different from the first and second biological conditions, and determining a recommendation for desirability of consumption of the food for the third biological condition. 67. The method of embodiment 66 further comprising comparing the recommendation for desirability of consumption of the food for the first, second, and third biological conditions to determine which, if any, is most restrictive, and determining a final recommendation for desirability of the food that is the most restrictive desirability. 68. The method of embodiment 66 further comprising performing one, two, or all of steps (i)-(iii) for a fourth biological condition, where the fourth biological condition is different from the first, second, and third biological conditions, and determining a recommendation for desirability of consumption of the food for the fourth biological condition. 69. The method of embodiment 68 further comprising comparing the recommendation for desirability of consumption of the food for the first, second, third, and fourth biological conditions to determine which, if any, is most restrictive, and determining a final recommendation for desirability of the food that is the most restrictive desirability. 70. The method of embodiment 68 further comprising performing one, two, or all of steps (i)-(iii) for a fifth biological condition, where the fifth biological condition is different from the first, second, third, and fourth biological conditions, and determining a recommendation for desirability of consumption of the food for the fifth biological condition. 71. The method of embodiment 70 further comprising comparing the recommendation for desirability of consumption of the food for the first, second, third, fourth, and fifth biological conditions to determine which, if any, is most restrictive, and determining a final recommendation for desirability of the food that is the most restrictive desirability. 72. The method of any of embodiments 57 through 71 further comprising determining a recommendation for desirability of consumption of a second food, wherein the second food is different from the first, comprising performing one, two, or all steps (i)-(iii) for the second food, for the first, second, third, fourth, or fifth condition, or any combination thereof. 73. The method of any of embodiments 57 through 72 wherein one, two, or all of steps (i)-(iii) are performed for at least 2, 5, 10, 20, 50, 100, 150, 200, 250, or 300 different foods. 74. The method of any of embodiments 57-73 wherein a food can be classed as part of a food group and the prediction of (i), (ii) and/or (iii) is based on the food group.

75. The method of any of embodiments 57-74 wherein the method further comprises providing an explanation for the recommendations for at least some of the foods to the individual, wherein the recommendation is determined from results of one or more steps of analysis of the food and its effect on one or more conditions of the individual. 76. The method of embodiment 75 wherein the explanation is provided as text suitable to layman understanding.

77. A list of food recommendations for an individual, wherein the recommendations are derived from predicting effects of each food on the list on one or more biological conditions of the individual, wherein the effects comprise one, two, or all of effects of macronutrient content of the food, effects of specific compound effect of the food, and effects of the food on the microbiome of the individual in relation to one or more biological conditions of the individual. 78. The list of embodiment 77 further comprising, for at least some of the foods, an explanation for the recommendation for the food, wherein the recommendation indicates one or more probable effects of macronutrient and/or specific compound content of the food and/or microbiome interaction with the food, on one or more of the biological conditions, or the effects of one or more conditions, in the individual. 79. The list of embodiment 78 wherein the explanation is in layman's terms. 80. The list of embodiment 77 wherein the list comprises at least 5, 10, 15, 20, 25, 30, 40, 50, 70, 100, 150, 200, 250, or 300 different food recommendations. 81. The list of embodiment 77 wherein each food on the list is designated a value according to its desirability for the individual. 82. The method of embodiment 81 wherein each food can have one of at least 2, 3, or 4 values for desirability. 83. The list of embodiment 82 wherein each food can have 4 values for desirability. 85. The list of embodiment 77 wherein the foods are chosen from the foods in Table 2.

86. A method of improving one or more biological conditions in an individual comprising (i) supplying the individual with food, supplement and/or ingredient recommendations, wherein the food, supplement and/or ingredient recommendations are based predicted effects of one or both of macronutrient content, specific compound content of the food or supplement on one or more biological conditions of the individual and, optionally, effect of the food on a microbiome of the individual; and (ii) altering the individual's food, supplement and/or ingredient consumption so that it more closely matches the food, supplement and/or ingredient recommendations. 87. The method of embodiment 86 wherein the one or more biological conditions of the individual are determined by analysis of phenotype information and microbiome information from the individual. 88. The method of embodiment 87 wherein the phenotype information is obtained in a process comprising determining responses for the individual to a questionnaire and microbiome information is obtained from a sample from the individual. 89. The method of embodiment 88 wherein the sample is a stool sample. 90. The method of embodiment 88 wherein the microbiome information comprises transcriptomic information. 91. The method of embodiment 88 wherein the microbiome information comprises taxonomic information and gene expression information. 92. The method of embodiment 88 wherein the food recommendations comprises a list of foods, each of which has a designation indicating desirability or undesirability of that food for the individual. 93. The method of embodiment 92 wherein the designation can have one of at least 2, 3, or 4 values. 94. The method of embodiment 86 wherein the food, supplement and/or ingredient recommendations are produced by a process comprising (i) selecting an individual set of biological conditions for the individual from an overall set of biological conditions based on the individual's phenotype and microbiome information; (ii) determining overall predicted desirability of foods, food groups, and/or supplements on at least part of the individual set of biological conditions for the individual; and (iii) from the results of (ii) determine the food, supplement and/or ingredient recommendations for the individual. 95. The method of any of embodiments 86 to 94 further comprising gathering information from the individual regarding phenotype and microbiome after the individual has implemented the recommendations for a period of time. 96. The method of embodiment 95 wherein the period of time is one week to one year. 97. The method of embodiment 95 further comprising altering the food, supplement and/or ingredient recommendations for the individual based on the phenotype and microbiome information gathered after the period of time. 98. The method of embodiment 86 wherein the microbiome information comprises information regarding one or more biochemical molecules in a sample from the individual. 99. The method of embodiment 98 wherein the one or more biochemical molecule are informative one or more biochemical activities. 100. The method of embodiment 98 wherein the information is obtained by a process comprising quantifying an enzymatic activity assay, a growth-inhibition culture, metabolic profiling, or any combination thereof 101. The method of embodiment 98 wherein the biochemical molecule is a small molecule, and wherein the small molecule comprises a metabolite generated by the biochemical activity. 102. The method of embodiment 101 wherein the small molecule comprises a short-chain fatty acid. 103. The method of embodiment 102 wherein the short-chain fatty acid comprises butyrate. 104. The method of embodiment 102 wherein the small molecule comprises propionate. 105. The method of embodiment 102 wherein the small molecule comprises a substrate of the biochemical activity.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The phrase "at least one" includes "one", "one or more", "one or a plurality" and "a plurality". The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3". The term "consisting essentially of" refers to the inclusion of recited elements and other elements that do not materially affect the basic and novel characteristics of a claimed combination.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
a) obtaining one or more biological samples from a subject;
b) extracting nucleic acids from the one or more biological sample;
c) processing the nucleic acids for RNA sequencing, thereby generating nucleic acid sequence data;
d) identifying, by a computer system, in the nucleic acid sequence data in electronic form a plurality of nucleic acids comprising a metatranscriptome of the subject;
e) obtaining phenotypic data about the subject in electronic form, the phenotypic data comprising a plurality of responses;
f) quantifying from the nucleic acid sequence data, one or more functional activity(ies) in the subject by:
1) associating, by the computer system, the plurality of nucleic acids of human origin or of microbial origin in the nucleic acid sequence data with a plurality of functional activity pathway scores, by combining and transforming a detected amount of the plurality of nucleic acids into the activity of the functional pathway;
2) associating the plurality of nucleic acids in the nucleic acid sequence data with a plurality of microbial taxa scores, by combining and transforming a detected amount of the plurality of nucleic acids into the activity of the taxa;
g) quantifying from the phenotypic data from the subject one or more phenotypic condition(s) in the subject by:
1) assigning a numerical value to each response in the plurality of responses comprising the phenotypic data, and
2) determining, for each phenotypic condition a phenotype score based on the numerical value;
h) using a recommendation engine of the computer system executing logic to produce a recommendation of one or more food item(s) in a plurality of food items for the subject based on the 1) functional activity pathway score, 2) the microbial taxa score; and the 3) phenotype score; and
i) outputting the recommendation to an electronic device;
j) consuming, by the subject, a food item that is outputted as desirable, or not consuming, by the subject, a food item that is outputted as least desirable.

2. The method of claim 1, wherein the subject is a human.

3. The method of claim 1, wherein one or more of the plurality of functional activity pathway scores is an integrative score based on a corresponding measure of transcriptional activity in the plurality of nucleic acids of human origin and/or of microbial origin for a respective KEGG ortholog designation in a plurality of KEGG ortholog designations.

4. The method of claim 1, wherein each functional activity in the one or more functional activity(ies) categories is independently selected from the group consisting of: a butyrate production pathway, an LPS biosynthesis pathway, a methane gas production pathway, a sulfide gas production pathway, a flagellar assembly pathway, an ammonia production pathway, a putrescine production pathway, an oxalate metabolism pathway, a uric acid production pathway, a salt stress pathway, a biofilm chemotaxis in virulence pathway, a TMA production pathway, a primary bile acid pathway, a secondary bile acid pathway, an acetate pathway, a propionate pathway, a branched chain amino acid pathway, a long chain fatty acid metabolism pathway, a long chain carbohydrate metabolic pathway, a cadaverine production pathway, a tryptophan pathway, a starch metabolism pathway, a fucose metabolism pathway, an inflammatory activity, a metabolic fitness, a digestive efficiency, an intestinal barrier health, a protein fermentation, a gas production, a microbial richness, a detoxification potential, a gut neuro-balance, a neurological health, a cardiovascular health, a hormonal balance, a musculoskeletal health, a hepatic function, a urogenital health, a mitochondrial activity, an immune function, a gastrointestinal health, diabetes, a skin condition, an infectious disease, a stress response, a mitochondrial health, a mitochondrial biogenesis, an oxidative stress, aging, and cellular senescence.

5. The method of claim 1, wherein: the plurality of functional activity pathway scores are associated with a corresponding threshold for the activity of the functional pathway, wherein when the functional activity pathway score does not satisfy the threshold that subject is identified as having a condition associated with the respective functional activity.

6. The method of claim 1, wherein the one or more phenotypic condition(s) is independently selected from the group consisting of abdominal weight, acne, attention deficit disorder, allergy, an ENT allergy, a respiratory allergy, a skin allergy, anxiety, an autoimmune disorder, a gut autoimmune condition, a joint autoimmune condition, a skin autoimmune condition, a cardiovascular condition, depression, a diverticular condition, dysbiosis, dysglycemia, dysmotility, and ENT condition, an eye condition, a female hormone condition, a food reaction, GERD, a GI inflammation, a headache condition, hypoglycemia, a hypothyroid condition, an infection condition, insomnia, leaky gut condition, a liver condition, a lung condition, a male hormone condition, a muscle condition, a nerve condition, a nutritional deficiency, obesity, overweight, a small intestinal bacterial overgrowth, and a thyroid condition.

7. The method of claim 1, wherein the plurality of food items comprises at least 100 food items.

8. The method of claim 1, wherein the plurality of food items comprises at least 10 supplements.

9. The method of claim 1, wherein the plurality of food items comprises at least 100 ingredients.

10. The method of claim 1, wherein the plurality of food items are associated with a plurality of rankings hierarchically arranged from least desirable to consume for the phenotypic condition or the functional activity to most desirable to consume for the phenotypic condition or the functional activity.

11. The method of claim 10, wherein the plurality of rankings is four rankings.

12. The method of claim 1, wherein the logic produces the recommendation of the one or more food items by first prioritizing rankings indicating a negative effect of the one or more foods item(s) on the one or more phenotypic condition, and second prioritizing rankings indicating a most beneficial effect of the one or more respective food item(s) on the one or more phenotypic condition or the functional activity category.

13. The method of claim 1, wherein:
the method further comprises:
determining, for each respective food item in the plurality of food items a predicted glycemic response by the subject based on the nucleic acid sequence data or the phenotypic data, and
determining, for the one or more food item(s) in the plurality of food items a corresponding glycemic response desirability ranking in a plurality of glycemic response desirability rankings; and
outputting the corresponding recommendation for each respective food item from the corresponding glycemic response desirability rating for the respective food item.

14. The method of claim 13, wherein the plurality of glycemic response desirability rankings consists of positive and negative.

15. The method of claim 13, wherein the glycemic response desirability ranking for each respective food item in the plurality of food items is determined by evaluating at least (i) a corresponding macronutrient profile for the respective food item, (ii) all or a portion of the nucleic acid sequence data, and (iii) all or a portion of the phenotypic data, using a machine learning model.

16. The method of claim 1, wherein:
The method further comprises, determining, for the one or more food item in the plurality of food items, whether the subject has a sensitivity for the one or more food item; and
outputting the corresponding recommendation for each respective food item by incorporating a sensitivity of the subject for the respective food item.

17. The method of claim 1, wherein the corresponding functional activity pathway score for a respective functional activity category is a non-integrative score based only on a corresponding measure of transcriptional activity from the detected amount of the nucleic acids associated with the one or more functional activity(ies).

\* \* \* \* \*